US010723787B2

(12) United States Patent
Perron et al.

(10) Patent No.: US 10,723,787 B2
(45) Date of Patent: Jul. 28, 2020

(54) METHODS FOR ALLEVIATING SYMPTOMS OF SPORADIC AMYOTROPHIC LATERAL SCLEROSIS BY NEUTRALIZING A HERV-K ENVELOPE PROTEIN USING AN ANTI-HERV-K ENVELOPE PROTEIN ANTIBODY

(71) Applicants: GENEURO SA, Plan-les-Ouates (CH); THE UNITED STATES OF AMERICA, as represented by the secretary, DEPARTMENT OF HEALTH AND HUMAN SERVICES, Bethesda, MD (US)

(72) Inventors: Hervé Perron, Saint Genis les Ollieres (FR); Julie Medina, Lentilly (CH); Avindra Nath, Silver Spring, MD (US); Joseph Perry Steiner, Mounty Airy, MD (US); Wenxue Li, Rockville, MD (US); Myound-Hwa Lee, Silver Spring, MD (US)

(73) Assignees: GENEURO SA, Plan-les-Oates (CH); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/478,576

(22) PCT Filed: Jan. 19, 2018

(86) PCT No.: PCT/US2018/014489
§ 371 (c)(1),
(2) Date: Jul. 17, 2019

(87) PCT Pub. No.: WO2018/136775
PCT Pub. Date: Jul. 26, 2018

(65) Prior Publication Data

US 2019/0345232 A1 Nov. 14, 2019

(30) Foreign Application Priority Data

Jan. 20, 2017 (EP) .................................... 17305062

(51) Int. Cl.
*G01N 33/53* (2006.01)
*A61K 49/00* (2006.01)
(Continued)

(52) U.S. Cl.
CPC ..... *C07K 16/1036* (2013.01); *G01N 33/6896* (2013.01); *A61K 39/12* (2013.01); *A61K 39/15* (2013.01); *A61K 39/245* (2013.01); *A61K 39/395* (2013.01); *A61K 39/42* (2013.01); *A61K 2039/505* (2013.01); *A61K 2039/525* (2013.01); *A61K 2039/60* (2013.01); *A61K 2039/6031* (2013.01); *A61K 2039/6075* (2013.01); *A61K 2121/00* (2013.01); *A61P 21/00* (2018.01); *A61P 25/00* (2018.01); *A61P 25/02* (2018.01); *A61P 25/14* (2018.01); *A61P 25/28* (2018.01); *A61P 31/00* (2018.01); *A61P 31/12* (2018.01); *A61P 31/14* (2018.01); *A61P 31/20* (2018.01); *A61P 31/22* (2018.01);
(Continued)

(58) Field of Classification Search
CPC ............ C12Q 2600/158; C12Q 1/6886; C12Q 2600/112; C12Q 1/702; C12Q 2600/118; A61K 39/0011; A61K 2039/505; A61K 38/17; A61K 39/00; A61K 39/12; A61K 2039/585; A61K 35/12; A61K 39/21; A61K 2039/507; A61K 38/162; A61K 38/1758; A61K 39/011; A61K 39/39558; A61K 39/42; A61P 37/00; A61P 31/12; A61P 25/28; A61P 35/00; C07K 2317/622; C07K 16/00; C07K 14/005; C07K 14/47; C07K 16/1036; C07K 2317/24; C07K 2317/33; C07K 2317/52; C07K 2317/76; C07K 2317/92; A01K 2217/206; A01K 2267/0318; C12N 2710/16122; C12N 2710/16222; C12N 2740/10022; C12N 2740/10033; C12N 2740/274; C12N 2740/12022; C12N 2720/12334; C12N 2740/12021; G01N 33/6896; G01N 2333/15; G01N 2333/705; G01N 2469/10; G01N 2469/20; G01N 2800/28; G01N 33/56983; G01N 33/57407
See application file for complete search history.

(56) References Cited

U.S. PATENT DOCUMENTS

2006/0160087 A1* 7/2006 McGrath ............. C12Q 1/6883 435/6.16
2019/0038659 A1* 2/2019 Nath ....................... A61P 25/28

FOREIGN PATENT DOCUMENTS

WO WO2004069174 * 8/2004
WO WO2010138803 * 12/2010 ............ C07K 16/30
(Continued)

OTHER PUBLICATIONS

Rudikoff et al., Proc Natl Acad Sci USA 1982; 79:1979-1983.*
(Continued)

*Primary Examiner* — Chang-Yu Wang
(74) *Attorney, Agent, or Firm* — W & C IP

(57) ABSTRACT

The present invention relates to a novel antibody against HERV-K envelope that targets a conserved region not affected by glycosylation or by native conformation, and its use in diagnostics and/or in therapy.

4 Claims, 9 Drawing Sheets

Figure 1:
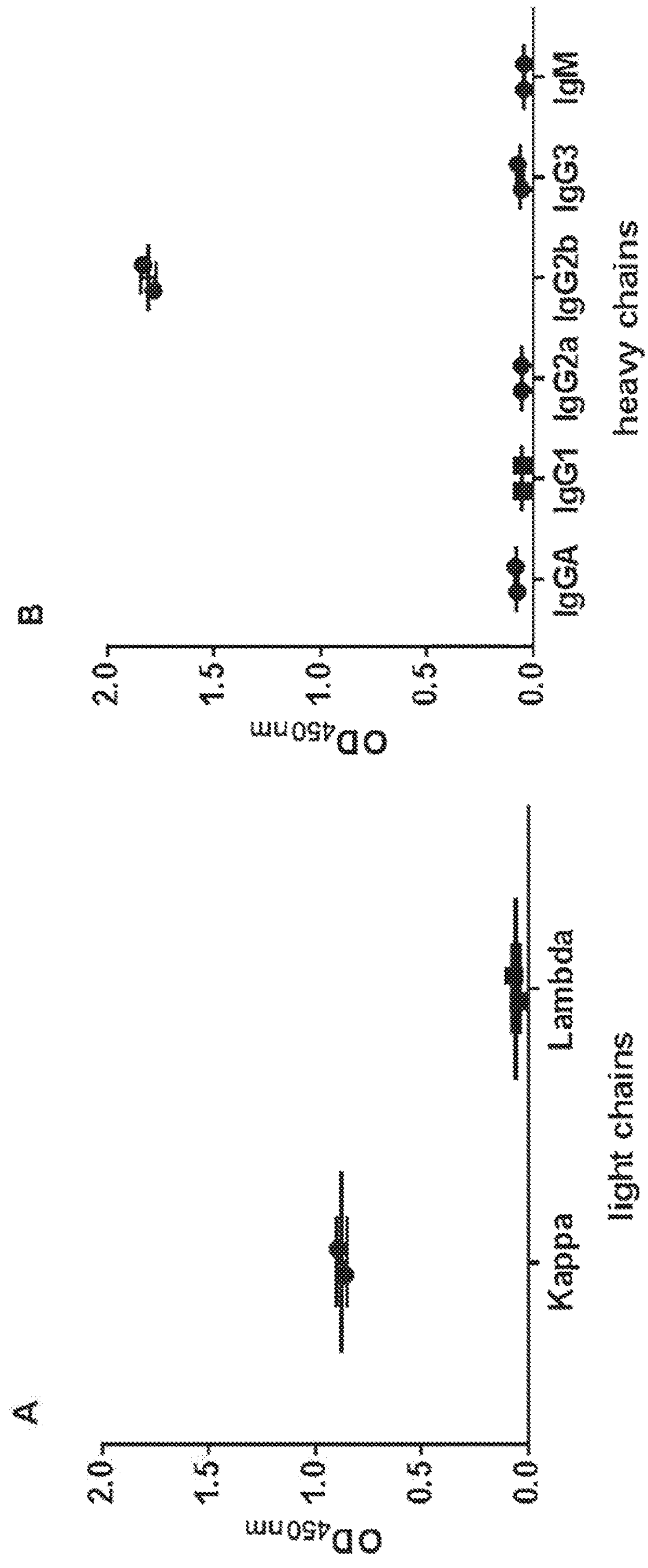

Specification includes a Sequence Listing.

(51) Int. Cl.

| | |
|---|---|
| ***A61K 49/16*** | (2006.01) |
| ***A61K 39/395*** | (2006.01) |
| ***A61K 39/00*** | (2006.01) |
| ***C12P 21/08*** | (2006.01) |
| ***C07K 16/00*** | (2006.01) |
| ***A61K 38/17*** | (2006.01) |
| ***C07K 14/47*** | (2006.01) |
| ***C07K 16/10*** | (2006.01) |
| ***G01N 33/68*** | (2006.01) |
| *A61P 31/22* | (2006.01) |
| *A61P 25/02* | (2006.01) |
| *A61P 25/28* | (2006.01) |
| *A61P 31/20* | (2006.01) |
| *A61P 25/00* | (2006.01) |
| *A61P 31/14* | (2006.01) |
| *A61P 21/00* | (2006.01) |
| *A61P 31/12* | (2006.01) |
| *G01N 33/563* | (2006.01) |
| *G01N 33/569* | (2006.01) |
| *A61P 31/00* | (2006.01) |
| *A61P 25/14* | (2006.01) |
| *A61K 39/42* | (2006.01) |
| *A61K 39/245* | (2006.01) |
| *A61K 39/12* | (2006.01) |
| *A61K 39/15* | (2006.01) |

(52) U.S. Cl.

CPC ...... *C07K 2317/00* (2013.01); *C07K 2317/10* (2013.01); *C07K 2317/34* (2013.01); *C07K 2317/50* (2013.01); *C07K 2317/62* (2013.01); *C07K 2317/622* (2013.01); *C07K 2317/624* (2013.01); *C07K 2317/64* (2013.01); *C07K 2317/66* (2013.01); *C07K 2317/70* (2013.01); *C07K 2317/76* (2013.01); *C12N 2320/00* (2013.01); *C12N 2320/50* (2013.01); *C12N 2710/00011* (2013.01); *C12N 2710/00022* (2013.01); *C12N 2710/16011* (2013.01); *C12N 2710/16122* (2013.01); *C12N 2740/10011* (2013.01); *C12N 2740/10022* (2013.01); *C12Q 2600/158* (2013.01); *G01N 33/53* (2013.01); *G01N 33/563* (2013.01); *G01N 33/569* (2013.01); *G01N 2333/15* (2013.01); *G01N 2469/00* (2013.01); *G01N 2469/10* (2013.01); *G01N 2800/00* (2013.01); *G01N 2800/28* (2013.01); *G01N 2800/285* (2013.01); *G01N 2800/52* (2013.01); *G01N 2800/56* (2013.01)

(56) References Cited

FOREIGN PATENT DOCUMENTS

WO 2013/059426 A1 4/2013
WO WO2013059426 * 4/2013 ............ A61K 39/42
WO 2018/044970 A1 3/2018
WO WO2018044970 * 3/2018 ............ C07K 16/10

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307:198-205.*
Vajdos et al., J. Mol. Med., 2002; 320: 415-428.*
Holm et al., Mol. Immunol., 2007; 44: 1075-1084.*
Chen et al., J. Mol. Bio., 1999; 293: 865-881.*
Wu et al.,J. Mol. Biol.,1999; 294: 151-162.*
Burgess et al., J of Cell Bio. 1990, 111:2129-2138.*
Bowie et al., Science, 1990, 247:1306-1310.*
Pawson et al., Science, 2003, 300:445-452.*
Alaoui-Ismaili et al., Cytokine Growth Factor Rev. 2009; 20:501-507.*
Guo et al., PNAS 2004; 101:9205-9210.*
Tam et al., Mobile DNA; 2019; 10:32, doi.org/10.1186/s13100-019-0176-1.*
Ragagnin et al. Front. Neurosci. 2019, doi: 10.3389/fnins.2019.00532.*
Saito et al., Circulation, 2017; 136:1920-1935. DOI:10.1161/Circulationaha.117.027589.*
Balestrieri et al., Front. Microbiol. 2018; doi:10.3389/fmicb.2018.01448.*
Chen et al. Oncogenesis 2019; 8:6, doi.org/10.1038/s41389-018-0114-y.*
The factsheet of amyotrophic lateral sclerosis from the NINDS website: www.ninds.nih.gov/Disorders/Patient-Caregiver-Education/Fact-Sheets/Amyotrophic-Lateral-Sclerosis-ALS-Fact-Sheet, published Jun. 2013, retrieved on Nov. 20, 2019.*
Picher-Martel et al. Acta Neuropathologica Communications; 2016; 4:70. DOI 10.1186/s40478-016-0340-5.*
Van Damme et al., Disease Models & Mechanisms, 2017; 10:537-549; doi:10.1242/dmm.029058.*
Ferraluolo et al., Nat. Rev. Neurol. 2011; 7:616-630; doi:10.1038/nmeruol.2011.152.*
Sica et al., Arq Neuropsiquiatr 2011; 69: 699-706.*
Schymick et al. Hum. Mol. Genet. 2007; 17: R233-R242.*
Li et al., Sci. Transl. Med., 2015; 7:307ra153307ra153.DOI:10.1126/scitranslmed.aac8201.*
Kury et al. Trends Mol. Med. 2018; 24:379-394. doi:10.1016/j.molmed.2018.02.007.*
Morrice et al. Neural Regen. Res. 2018; 13:2050-2054.doi:10.4103/1673-5374.241445.*
Philips and Rothstein, Rodent Models of amyotrophic lateral sclerosis: Curr. Protoc. Pharmacol. 2015; 69:5.67.1-5.67.21. doi: 10.1002/0471141755.ph0567s69.*
Douville et al. Front. Microbiol. 2017; 8:1986. doi:10.3389/fmicb.2017.01986.*
Li et al: "Human endogenous retrovirus-K contributes to motor neuron disease", Science Translational Medicine, vol. 7, No. 307, Sep. 30, 2015.

* cited by examiner

A: GN_mAb_Env_K01 light variable chain

DVVMTQTPLTLSVTIGQPASISCKSSQSLLDSDGKTYLNWLLQRPGESPKLLIYLVSKLDSGVPDRFTGSGSGTDFTLKISRV

EAEDLGVYYC*LQATHFPWT*FGGGTKLEIK*RADAAPTVSIFPPSSEQLTSGGASARVLR* SEQ ID NO. 11

B: GN_mAb_Env_K01 heavy variable chain

QVQLQQPGAELVRPGASVKLSCKASGYTFTSYWMNWVKQRPEQGLEWIGRIDPYDSETHYNQKFKDKAILTVDKSSSTAYMQL

SSLTSEDSAVYYC*ASLYYYGISL*WGQGTLVTVS*AAKTTPPSVYPLAPGCGDTTGSSVTLGCLVKGYFPESVTVTWNSGSLS*

SEQ ID NO. 12

FIG.2

SEQUENCE LISTING

```
<160> NUMBER OF SEQ ID NOS: 13

<210> SEQ ID NO 1
<211> LENGTH: 11
<212> TYPE: PRT
<213> ORGANISM: Mus musculus

<400> SEQUENCE: 1

Gln Ser Leu Leu Asp Ser Asp Gly Lys Thr Tyr
1               5                   10


<210> SEQ ID NO 2
<211> LENGTH: 3
```

<212> TYPE: PRT
<213> ORGANISM: Mus musculus

<400> SEQUENCE: 2

Leu Val Ser
1

<210> SEQ ID NO 3
<211> LENGTH: 9
<212> TYPE: PRT
<213> ORGANISM: Mus musculus

<400> SEQUENCE: 3

Leu Gln Ala Thr His Phe Pro Trp Thr
1 5

<210> SEQ ID NO 4
<211> LENGTH: 8
<212> TYPE: PRT
<213> ORGANISM: Mus musculus

<400> SEQUENCE: 4

Gly Tyr Thr Phe Thr Ser Tyr Trp
1 5

<210> SEQ ID NO 5
<211> LENGTH: 8
<212> TYPE: PRT
<213> ORGANISM: Mus musculus

<400> SEQUENCE: 5

Ile Asp Pro Tyr Asp Ser Glu Thr
1 5

<210> SEQ ID NO 6
<211> LENGTH: 10
<212> TYPE: PRT
<213> ORGANISM: Mus musculus

<400> SEQUENCE: 6

Ala Ser Leu Tyr Tyr Tyr Gly Ile Ser Leu
1 5 10

<210> SEQ ID NO 7
<211> LENGTH: 112
<212> TYPE: PRT
<213> ORGANISM: Mus musculus

<400> SEQUENCE: 7

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Ser
20 25 30

Asp Gly Lys Thr Tyr Leu Asn Trp Leu Leu Gln Arg Pro Gly Glu Ser
35 40 45

Pro Lys Leu Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Leu Gln Ala
85 90 95

Thr His Phe Pro Trp Thr Phe Gly Gly Gly Thr Lys Leu Glu Ile Lys 100 105 110

<210> SEQ ID NO 8
<211> LENGTH: 116
<212> TYPE: PRT
<213> ORGANISM: Mus musculus

<400> SEQUENCE: 8

Gln Val Gln Leu Gln Gln Pro Gly Ala Glu Leu Val Arg Pro Gly Ala
1 5 10 15

Ser Val Lys Leu Ser Cys Lys Ala Ser Gly Tyr Thr Phe Thr Ser Tyr
20 25 30

Trp Met Asn Trp Val Lys Gln Arg Pro Glu Gln Gly Leu Glu Trp Ile
35 40 45

Gly Arg Ile Asp Pro Tyr Asp Ser Glu Thr His Tyr Asn Gln Lys Phe
50 55 60

Lys Asp Lys Ala Ile Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Ser Leu Tyr Tyr Tyr Gly Ile Ser Leu Trp Gly Gln Gly Thr Leu
100 105 110

Val Thr Val Ser
115

<210> SEQ ID NO 9
<211> LENGTH: 15
<212> TYPE: PRT
<213> ORGANISM: Homo sapiens

<400> SEQUENCE: 9

Ser Leu Asp Lys His Lys His Lys Lys Leu Gln Ser Phe Tyr Pro
1 5 10 15

<210> SEQ ID NO 10
<211> LENGTH: 9
<212> TYPE: DNA
<213> ORGANISM: Mus musculus

<400> SEQUENCE: 10 ccctctccc 9

<210> SEQ ID NO 11
<211> LENGTH: 141
<212> TYPE: PRT
<213> ORGANISM: Mus musculus

<400> SEQUENCE: 11

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Ser
20 25 30

Asp Gly Lys Thr Tyr Leu Asn Trp Leu Leu Gln Arg Pro Gly Glu Ser
35 40 45

Pro Lys Leu Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Leu Gln Ala

-continued

```
                85                  90                  95

Thr His Phe Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Ala Arg Val Leu Arg
    130                 135                 140


<210> SEQ ID NO 12
<211> LENGTH: 164
<212> TYPE: PRT
<213> ORGANISM: Mus musculus

<400> SEQUENCE: 12

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Leu Tyr Tyr Tyr Gly Ile Ser Leu Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser


<210> SEQ ID NO 13
<211> LENGTH: 543
<212> TYPE: PRT
<213> ORGANISM: Homo sapiens

<400> SEQUENCE: 13

Leu Pro Met Pro Ala Gly Ala Ala Ala Ala Asn Tyr Thr Tyr Trp Ala
1               5                   10                  15

Tyr Val Pro Phe Pro Pro Leu Ile Arg Ala Val Thr Trp Met Asp Asn
            20                  25                  30

Pro Thr Glu Val Tyr Val Asn Asp Ser Val Trp Val Pro Gly Pro Ile
        35                  40                  45

Asp Asp Arg Cys Pro Ala Lys Pro Glu Glu Glu Gly Met Met Ile Asn
    50                  55                  60

Ile Ser Ile Gly Tyr His Tyr Pro Pro Ile Cys Leu Gly Arg Ala Pro
65                  70                  75                  80

Gly Cys Leu Met Pro Ala Val Gln Asn Trp Leu Val Glu Val Pro Thr
                85                  90                  95

Val Ser Pro Ile Cys Arg Phe Thr Tyr His Met Val Ser Gly Met Ser
            100                 105                 110
```

-continued

```
Leu Arg Pro Arg Val Asn Tyr Leu Gln Asp Phe Ser Tyr Gln Arg Ser
        115                 120                 125

Leu Lys Phe Arg Pro Lys Gly Lys Pro Cys Pro Lys Glu Ile Pro Lys
    130                 135                 140

Glu Ser Lys Asn Thr Glu Val Leu Val Trp Glu Glu Cys Val Ala Asn
145                 150                 155                 160

Ser Ala Val Ile Leu Gln Asn Asn Glu Phe Gly Thr Ile Ile Asp Trp
                165                 170                 175

Ala Pro Arg Gly Gln Phe Tyr His Asn Cys Ser Gly Gln Thr Gln Ser
            180                 185                 190

Cys Pro Ser Ala Gln Val Ser Pro Ala Val Asp Ser Asp Leu Thr Glu
        195                 200                 205

Ser Leu Asp Lys His Lys His Lys Lys Leu Gln Ser Phe Tyr Pro Trp
    210                 215                 220

Glu Trp Gly Glu Lys Gly Ile Ser Thr Pro Arg Pro Lys Ile Val Ser
225                 230                 235                 240

Pro Val Ser Gly Pro Glu His Pro Glu Leu Trp Arg Leu Thr Val Ala
                245                 250                 255

Ser His His Ile Arg Ile Trp Ser Gly Asn Gln Thr Leu Glu Thr Arg
            260                 265                 270

Asp Arg Lys Pro Phe Tyr Thr Ile Asp Leu Asn Ser Ser Leu Thr Val
        275                 280                 285

Pro Leu Gln Ser Cys Val Lys Pro Pro Tyr Met Leu Val Val Gly Asn
    290                 295                 300

Ile Val Ile Lys Pro Asp Ser Gln Thr Ile Thr Cys Glu Asn Cys Arg
305                 310                 315                 320

Leu Leu Thr Cys Ile Asp Ser Thr Phe Asn Trp Gly His Arg Ile Leu
                325                 330                 335

Leu Val Arg Ala Arg Glu Gly Val Trp Ile Pro Val Ser Met Asp Arg
            340                 345                 350

Pro Trp Glu Ala Ser Pro Ser Val His Ile Leu Thr Glu Val Leu Lys
        355                 360                 365

Gly Val Leu Asn Arg Ser Lys Arg Phe Ile Phe Thr Leu Ile Ala Val
    370                 375                 380

Ile Met Gly Leu Ile Ala Val Thr Ala Thr Ala Ala Val Ala Gly Val
385                 390                 395                 400

Ala Leu His Ser Ser Val Gln Ser Val Asn Phe Val Asn Asp Trp Gln
                405                 410                 415

Lys Asn Ser Thr Arg Leu Trp Asn Ser Gln Ser Ser Ile Asp Gln Lys
            420                 425                 430

Leu Ala Asn Gln Ile Asn Asp Leu Arg Gln Thr Val Ile Trp Met Gly
        435                 440                 445

Asp Arg Leu Met Ser Leu Glu His Arg Phe Gln Leu Gln Cys Asp Trp
    450                 455                 460

Asn Thr Ser Asp Phe Cys Ile Thr Pro Gln Ile Tyr Asn Glu Ser Glu
465                 470                 475                 480

His His Trp Asp Met Val Arg Arg His Leu Gln Gly Arg Glu Asp Asn
                485                 490                 495

Leu Thr Leu Asp Ile Ser Lys Leu Lys Glu Gln Ile Phe Glu Ala Ser
            500                 505                 510

Lys Ala His Leu Asn Leu Val Pro Gly Thr Glu Ala Ile Ala Gly Val
        515                 520                 525
```

-continued

```
Ala Asp Gly Leu Ala Asn Leu Asn Pro Val Thr Trp Val Lys Thr
    530                 535                 540
```

METHODS FOR ALLEVIATING SYMPTOMS OF SPORADIC AMYOTROPHIC LATERAL SCLEROSIS BY NEUTRALIZING A HERV-K ENVELOPE PROTEIN USING AN ANTI-HERV-K ENVELOPE PROTEIN ANTIBODY

CROSS-REFERENCE TO RELATED APPLICATIONS

This application is a national stage filing from PCT/US2018/014489 filed on Jan. 19, 2018, which claims priority to European Application 17305062.6 filed Jan. 20, 2017.

FIELD OF THE INVENTION

The present invention relates to a novel antibody against HERV-K envelope that targets a conserved region not affected by glycosylation or by native conformation, and its use in diagnostics and/or in therapy.

BACKGROUND OF THE INVENTION

Amyotrophic lateral sclerosis (ALS) disease was first described by the French neurologist to Jean-Martin Charcot and its name reflects both the degeneration of corticospinal motor neurons, the descending axons of which show altered structure in the lateral spinal cord (lateral sclerosis) and the demise of spinal motor neurons, with secondary denervation associated with muscle wasting (amyotrophy) (Taylor, Brown, and Cleveland 2016). Indeed, ALS is a progressive and ultimately fatal neurodegenerative disease resulting from motor neuron degeneration in the cerebral motor cortex, the brainstem and spinal cord involved in the planning, control and execution of voluntary movements. Fatal outcome typically occurs 3-5 years after diagnosis (Taylor, Brown, and Cleveland 2016). The prevalence of ALS approximately reaches 5 cases in 100 000, which reflects the rapid lethality of the disease (Taylor, Brown, and Cleveland 2016). About 10% of ALS cases appear to be genetically transmitted in families (hereditary ALS), in association with specific genomic mutations. For example, approximately 20%/o of familial ALS is associated with a mutation in the superoxide dismutase (sod1) gene (Vucic and Kiernan 2009; Rosen 1993). Other non-familial cases are classified as sporadic ALS (90% of ALS cases) (Lagier-Tourenne and Cleveland 2009), meaning that it occurs without a family history.

Neurodegenerative disorders, such as Parkinson's, Huntington's, Alzheimer's disease, frontotemporal lobar degeneration (FTLD) and ALS are associated with the accumulation of misfolded proteins both inside and outside of neuronal and glial cells in the central nervous system (Polymenidou and Cleveland 2011). These misfolded protein aggregates are pathological hallmarks of each disease and can spread from cell to cell through a prion-like mechanism after an initiating event. One widely held view is that these aggregates play a critical role in disease initiation and progression, with the misfolded versions of endogenous proteins likely to acquire toxic properties, potentially through increased hydrophobicity and/or sequestration of essential cellular components within the aggregates, generation of oxidative species, proteasome inhibition and through other pathways. An alternative view is that the large aggregates do not represent the toxic form, but the final product of a defensive cell response aimed at protecting cells from more toxic oligomeric species that remain undetectable by most techniques (Polymenidou and Cleveland 2011).

Studies of serum samples from patients with ALS, but seronegative for Human Immunodeficiency Virus (HIV) or Human T cell leukemia virus (HTLV) exogenous viruses, showed reverse transcriptase (RT) activity in 50-60% of ALS samples with level comparable to those of HIV-infected patients (MacGowan et al. 2007; McCormick et al. 2008; Andrews et al. 2000; Steele et al. 2005). This is consistent with the fact that retroviral involvement has been suspected for several years since the recognition that both murine and human retroviruses can cause ALS-like syndromes (McCormick et al. 2008). ALS-like disorder in HIV-positive patients can remit with antiretroviral therapy (Moulignier et al. 2001; von Giesen et al. 2002). This is valid for ALS symptomatology in HIV-infected patients and may nonetheless represent a peculiar sub-category of ALS cases.

Increased RT activity was also found in serum of ALS patient's first degree relatives, which leads to the speculation that RT activity may derive from inherited active copies among human endogenous retroviruses (HERVs), which represent 8% of our genome (Steele et al. 2005).

Nonetheless, the detection of RT activity as such in ALS does not identify the origin of this enzyme, but the involvement of HERV-K in post-monrtem brain, (Douville et al. 2011)] has been shown. Sequencing studies revealed that the 7q34 and 7q36.1 chromosomal loci (corresponding to HML-2 and HML-3 subfamilies of HERV-K respectively) are more frequently expressed in patients with ALS, compared to controls (Douville and Nath 2014). Moreover, it has been recently observed that both HERV-K gag-pol and env RNA have significantly elevated expression in brains from ALS patients compared to controls (Li et al. 2015).

Expression of HERV-K in human neuronal cultures caused neuronal cytotoxicity, as observed by the decreased number of neurons and also the retraction of neurites in a dose dependent manner after the transfection of the entire HERV-K genome or of the HERV-K-env gene only. This suggested that intracellular HERV-K-Env protein could contribute to neurotoxicity. This has been confirmed by the CRISP/casp9 assay which has permitted HERV-K twofold increased expression through its LTR activation by the VP64 transcription factor (Li et al. 2015). HERV-K expression causes in vivo loss of the motor cortex volume in transgenic mice expressing the HERV-K-env gene in cortical neurons which is independent of the immune reactivity as measured with the ionized calcium-binding adapter molecule 1 (Iba-1) marker for microglia (Li et al. 2015). Behavioral analyses revealed that HERV-K-env transgenic mice traveled shorter distances, rested for longer periods and fell faster in a rotarod performance test displaying evidence of spasticity with increased clasping of the hind limbs. In addition to these motor dysfunctions, transgenic mice developed profound weakness of the limbs and spinal muscles including those for respiration resulting in 50% mortality by 10 months (Li et al. 2015).

Interestingly, HERV-K RT expression correlated with increased TDP-43 levels in neurons from ALS patients, suggesting that RT expression occurs in combination with other aberrant cellular processes characteristic of the disease (Buratti and Baralle 2009; Geser et al. 2009; Douville et al. 2011). Evidence for such a prion-like mechanism in ALS now involves the main misfolded proteins, SOD1 and TDP-43 (Polymenidou and Cleveland 2011). Recently, Li and al demonstrated that TDP-43 could activate HERV-K-env expression in human neuron, which is consistent with their observation that TDP-43 can bind to the region 726-

CCCTCTCCC-734 (SEQ ID NO: 10) of HERV-K long terminal repeat (LTR) (Li et al. 2015). They also showed that endogenous TDP-43 silencing decreased HERV-K expression. These results have recently been complemented by showing that normal TDP-43 has no effect on HERV-K transcription in human astrocytes and neurons in vim), whereas TDP-43 has a binding site in the US region of HERV-K promoter. The latter binding is enhanced with inflammation, e.g. in presence of Tumor Necrosis Factor (TNF.alpha.), or with proteasome inhibition (Manghera, Ferguson-Parry, and Douville 2016). Interestingly, the same study showed that overexpression of aggregating forms of TDP-43 enhanced HERV-K viral protein expression and accumulation, when wild-type (normal) TDP-43 did not (Manghera, Ferguson-Parry, and Douville 2016). Moreover, despite evidence of enhanced stress granule and autophagic response in ALS cortical neurons, these cells failed to clear the excess HERV-K protein accumulation. Typical of most retroviral restriction factors, the TDP-43 promoter is likely to respond to interferon- and inflammation-associated transcription factors, as it contains binding sites for interferon regulatory factors (IRF1, IRF3) and nuclear factor-kappa B (NF.kappa.B) (Douville et al. 2011).

Taken together, these findings suggest that endogenous retroviral elements and HERV-K in particular are involved in the pathophysiology of ALS and could be the missing link between TDP43 and this proteinopathy (Alfahad and Nath 2013). HERV-K envelope protein expression within neurons of patients with ALS can therefore contribute to the neurodegeneration and disease pathogenesis.

To date, as a symptomatic treatment, Riluzole remains the only relatively effective drug and only extends the average survival of patients by 3-6 months (Hardiman, van den Berg, and Kieman 2011). Present treatment protocols are based on symptom management and on preservation of quality of life, provided in a multidisciplinary setting. The discovery of an efficient therapy remains a critical need for patients with this rapidly fatal disease (Hardiman, van den Berg, and Kiernan 2011).

Consequently, there remains an unmet need for effective therapeutic agents for treating ALS.

SUMMARY OF THE INVENTION

The inventors have developed a novel antibody against the HERV-K envelope protein that displays unexpected properties.

The inventors have shown that the antibody according to the present invention, named GN_mAb_Env_K01, is a murine monoclonal antibody (mAb) that selectively binds to the SLDKHKHKKLQSFYP (SEQ ID NO:9) linear epitope on the surface of the HERV-K-Env protein. GN_mAb_Env_K01 is a full-length antibody of the IgG2b/kappa murine subclass. GN_mAb_Env_K01 biological activity has been confirmed in ELISA and Western Blotting immunoassays. Surprisingly GN_mAb_Env_K01 recognized both the native and the denatured HERV-K-Env protein, but also the non-glycosylated and the glycosylated forms while the commercial anti-HERV-K-Env antibody failed to detect the glycosylated form.

Moreover and most unexpectedly, the targeted epitope appeared to be highly conserved with a stable amino acid sequence in HERV-K env genes described in the databases. This confers a unique positioning to this antibody, whatever the HERV-K copy involved in a pathogenic expression of its envelope protein. These unexpected results indicate that GN_mAb_Env_K01 is an original tool for targeting HERV-K envelope proteins. They also show that selecting and obtaining such a monoclonal antibody could not be foreseen or predicted by a given protocol of immunization, even for skilled persons.

Thus, the present invention relates to an antibody that recognizes the HERV-K Envelope protein, wherein said antibody binds to the epitope SLDKHKHKKLQSFYP (SEQ ID NO:9).

The invention also relates to an antibody that recognizes the HERV-K Envelope protein, wherein said antibody binds to the epitope SLDKHKHKKLQSFYP (SEQ ID NO:9) for use in therapy.

The invention also relates to an antibody that recognizes the HERV-K Envelope protein, wherein said antibody binds to the epitope SLDKHKHKKLQSFYP (SEQ ID NO:9) for use in a method for treating amyotrophic lateral sclerosis (ALS), preferably sporadic ALS.

In another aspect, the invention relates to a pharmaceutical composition comprising the antibody as defined above and a pharmaceutically acceptable excipient.

In another aspect, the invention also relates to a method for detecting the HERV-K envelope protein in a biological sample comprising the step of contacting said biological sample with an anti-HERV-K envelope antibody as defined above.

In another aspect, the invention also relates to a method for diagnosing ALS, notably sporadic ALS, in a patient comprising the step of contacting a biological sample obtained from said patient with an anti-HERV-K envelope antibody as defined above.

DETAILED DESCRIPTION

Definitions

As used herein, the term "treating" or "treatment" means reversing, alleviating, inhibiting the progress of the disorder or condition to which such term applies.

As used herein, the term "prevention" refers to preventing the disease or condition from occurring in a subject which has not yet presented clinical symptoms, typical lesions or to physiological dysfunctions that would allow its clinical diagnosis.

As used herein, "antibody" or "immunoglobalin" have the same meaning, and will be used equally in the present invention. The term "antibody" as used herein refers to immunoglobulin molecules and immunologically active portions of immunoglobulin molecules, i.e., molecules that contain an antigen binding site that specifically binds an antigen. As such, the term "antibody" encompasses not only whole antibody molecules, but also antibody fragments, as well as derivatives of antibodies.

As used herein, the expression "fragment of antibody" refers to a portion of such an antibody that mimics the hypervariable region, such as a CDR (CDR-L1, CDR-L2, CDR-L3, CDR-H1, CDR-H2, CDR-H3). The fragments of antibody according to the present invention retain the binding affinity and specificity of said antibody. Such fragments are functional equivalents of said antibody and they bind at substantially the same epitope as said antibody. Examples of fragments of antibody include but are not limited to heavy chain, light chain, VL, VH, Fv, Fab, Fab', F(ab)2, and F(ab')2.

As used herein, the expression "derivative of antibody" refers to a fragment of the antibody of the invention, preferably including at least one CDR of said antibody, preferably at least one CDR3 of said antibody, fused to at least one sequence different from the natural sequence (e.g. a linker sequence of another species . . . ), said derivative having binding affinity and specificity to HERV-K Env comparable to that of the antibody of the invention. The derivatives according to the present invention retain the binding affinity and specificity of said antibody. Such derivatives are functional equivalents of said antibody and they bind at substantially the same epitope as said antibody. Examples of derivatives of antibody include, but are not limited to scFv, (scFv)2 and diabodies.

In natural antibodies, two heavy chains (HC) are linked to each other by disulfide bonds and each heavy chain is linked to a light chain (LC) by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains.

Typically, the light chain includes two domains, a variable domain (VL) and a constant domain (CL). The heavy chain includes four domains, a variable domain (VH) and three constant domains (CH1, CH2 and CH3, collectively referred to as (CH). The variable regions of both light (VL) and heavy (VH) chains determine the binding site specific to the antigenic epitope. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists in the variable portions of one light chain and one heavy chain. The specificity of the antibody resides in the structural complementarity between the antibody binding site and the antigenic epitope. Antibody binding sites are made up of residues that are primarily from the hypervariable or complementarity determining regions (CDRs). Occasionally, residues from non-hypervariable or framework regions (FR) influence the overall domain structure and hence the binding site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used herein, the term "chimeric antibody" refers to an antibody which comprises a VH domain and a VL domain of an antibody from any species, preferably mouse, and a CH domain and a CL domain of a human antibody.

According to the invention, the term "humanized antibody" refers to an antibody having variable region framework and constant regions from a human antibody but retains the CDRs of an antibody from any species, preferably mouse.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

As used herein, The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

As used herein, The term "Fab'" refers to an antibody fragment having a molecular weight of about 50,000) and antigen binding activity, which is obtained by cutting a disulfide bond of the hinge region of the F(ab')2.

The expressions "A single chain Fv" or "scFv" refer to a polypeptide, which is a covalently linked VH::VL heterodimer, and usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

As used herein, the expression "antibody of the invention" refers to an antibody directed against, i.e. that specifically binds to, HERV-K Envelope protein (HERV-K Env), preferably against HERV-K Envelope protein of the type-K human endogenous retrovirus family (HERV-K), more preferably against the epitope as set forth in SEQ ID NO:9.

As used herein, the term "biological sample" as used herein refers to any biological sample obtained for the purpose of evaluation in vitro. In the present invention, the sample or patient sample may comprise any body fluid or disease-specific tissue and lesions, such as biopsies. Examples of body fluid include blood, serum, plasma, nipple aspirate fluid, urine, saliva, synovial fluid and cerebrospinal fluid (CSF).

Typically an antibody of the invention protects human neuronal cells from cytotoxicity induced by neuronal exposure to HERV_K Env protein.

More particularly, an antibody of the invention preferably exhibits one or more of the following functional characteristics:

it preserves neuronal functional activity of neurons exposed to HERV K Env protein;

it preserves cell viability of neurons exposed to HERV_K Env protein; and/or it preserves neuronal morphology of neurons exposed to HERV_K Env protein.

A protective effect of an antibody according to the invention on neuronal functional activity against extracellular HERV-K envelope cytotoxicity may be assessed in vitro as illustrated in example 2 of the present invention (see point 2.1.3). In particular, such effect may be assessed by recording spontaneous electrophysiological activity of human neurons in vitro, following treatment with the recombinant HERV-K Env protein. Thus, typically treatment with an antibody of the invention restores the spontaneous activity of human neurons exposed to the recombinant HERV-K Env protein, by at least 50%, notably at least 60%, at least 70%, at least 80%, at least 90% or at least 95% when compared to human neurons un-treated with said recombinant HERV-K Env protein.

In some embodiment, the protective effect of an antibody of the invention may be alternatively or additionally assessed in vitro by analyzing neuronal culture viability after treatment with the recombinant HERV-K Env protein, as for example illustrated in example 2 (see point 2.1.1). Typically in such an embodiment, treatment with an antibody of the invention increases the viability of human neurons pre-incubated with the recombinant HERV-K Env protein by at least by at least 20%, when compared to the viability of human neurons un-treated with said antibody of the invention.

In some embodiment, the protective effect of an antibody of the invention may be alternatively or additionally assessed in vitro, by estimating the neuronal morphology (such as for example the neurite length) of human neurons in culture after treatment with the recombinant HERV-K Env protein, as for example illustrated in example 2 (see point 2.1.2). Typically in such an embodiment, treatment with an antibody of the invention increases the neurite length of human neurons pre-incubated with the recombinant HERV-K Env protein by at least 20% as compared to the viability of human neurons un-treated with said antibody of the invention.

In one embodiment, the antibody of the invention comprises each of the 6 CDRs as depicted in SEQ ID No: 1, SEQ ID No: 2, SEQ ID No: 3, SEQ ID No: 4, SEQ ID No: 5, and SEQ ID No: 6.

In one embodiment, the antibody of the invention comprises:

- a light chain wherein the variable domain comprises each of the 3 CDRs as depicted in SEQ ID No: 1 for CDR-L1, SEQ ID No: 2 for CDR-L2 and SEQ ID No: 3 for CDR-L3; and
- a heavy chain wherein the variable domain comprises each of the 3CDRs as depicted in SEQ ID No: 4 for CDR-H1, SEQ ID No: 5 for CDR-H2 and SEQ ID No: 6 for CDR-H3.

TABLE 1

CDR domains of an antibody according to the invention

| Domains | SEQ ID No: | Sequence |
|---|---|---|
| CDR-L1 | 1 | QSLLDSDGKTY |
| CDR-L2 | 2 | LYS |
| CDR-L3 | 3 | LQATHFPWT |
| CDR-H1 | 4 | GYTFTSYW |
| CDR-H2 | 5 | IDPYDSET |
| CDR-H3 | 6 | ASLYYYGISL |

In one embodiment, the antibody, fragment or derivative of the invention comprises:

- a light chain variable region (VL) as depicted in SEQ ID No: 7; and
- a heavy chain variable region (VH) as depicted in SEQ ID No: 8.

The above mentioned light and heavy variable regions are disclosed in Table 2:

TABLE 2

Light and heavy variable regions of an antibody according to the invention

| Domains | SEQ ID No: | Sequence |
|---|---|---|
| VL | 7 | DVVMTQTPLTLSVTIGQPASISCKSSQSLLDSDGKTYLNWLLQRPGESPKLLIYLVSKLDSGVPDRFTGSGSGTDFTLKISRVEAEDLGVYYCLQATHFPWTFGGGTKLEIK |
| VH | 8 | QVQLQQPGAELVRPGASVKLSCKASGYTFTSYWMNWVKQRPEQGLEWIGRIDPYDSETHYNQKFKDKAILTVDKSSSTAYMQLSSLTSEDSAVYYCASLYYYGISLWGQGTLVTVS |

In one embodiment, the antibody, fragment or derivative of the invention is selected from the group consisting of a Fv, Fab, F(ab')2, Fab', dsFv, scFv, sc(Fv)2, a diabody, and multispecific antibodies formed from antibody fragments.

In a preferred embodiment, the antibody of the invention is a monoclonal antibody. Monoclonal antibodies of the invention are monovalent, bivalent, multivalent, monospecific, bispecific, or multispecific. In another embodiment, the antibody directed against HERV-K Env is a binding fragment or a conjugate. For examples antibodies of the invention may be conjugated to a growth inhibitory agent, cytotoxic agent, or a prodrug-activating enzyme.

Another type of amino acid modification of the antibody of the invention may be useful for altering the original glycosylation pattern of the antibody. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

In another embodiment, the antibody of the invention is a monoclonal humanized antibody, more preferably an IgG4 humanized monoclonal antibody.

Said humanized antibody may be produced by obtaining nucleic acid sequences encoding for CDRs domain by inserting them into an expression vector for animal cell having genes encoding a heavy chain constant region identical to that of a human antibody; and a light chain constant region identical to that of a human antibody, and expressing the expression vector by introducing it into an animal cell. The humanized antibody expression vector may be either of a type in which a gene encoding an antibody heavy chain and a gene encoding an antibody light chain exist on separate vectors or of a type in which both genes exist on the same vector (tandem type). In respect of easiness of construction of a humanized antibody expression vector, easiness of introduction into animal cells, and balance between the expression levels of antibody H and L chains in animal cells, a tandem type of the humanized antibody expression vector is more preferable. Examples of the tandem type humanized antibody expression vector include pKANTEX93, pEE 18 and the like. Methods for producing humanized antibodies based on conventional recombinant DNA and gene transfection techniques are well known in the art. Antibodies can be humanized using a variety of techniques known in the art including, for example, CDR-grafting, veneering or resurfacing, and chain shuffling. The general recombinant DNA technology for preparation of such antibodies is also known.

Thus, an embodiment of the invention relates to a monoclonal humanized antibody comprising:

- a light chain wherein the variable domain comprises each of the 3 CDRs as depicted in SEQ ID No: 1 for CDR-L1, SEQ ID No: 2 for CDR-L2 and SEQ ID No: 3 for CDR-L3; and
- a heavy chain wherein the variable domain comprises each of the 3CDRs as depicted in SEQ ID No: 4 for CDR-H1, SEQ ID No: 5 for CDR-H2 and SEQ ID No: 6 for CDR-H3.

Pharmaceutical Composition

A further object of the invention relates to a pharmaceutical composition comprising an effective dose of an antibody directed against HERV-K Envelope protein (HERV-K Env) and a pharmaceutically acceptable excipient.

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intrathecal (directly in the cerebrospinal fluid), intramuscular or subcutaneous administration and the like.

In some embodiments, compositions formulated for intrathecal administration may be of particular advantage. Indeed, such administration mode may allow short-term administration of a non-human antibody, such as a mouse antibody, or a chimeric antibody in specific therapeutic strategies. Indeed, the "immune-privileged" physiology of the CNS allows tolerance that is not possible with administration via systemic routes. Thus the intrathecal injection mode is a common neurological and neurosurgical practice. For example, rituximab is a mouse-human chimeric antibody which has been used intrathecally in patients with multiple sclerosis and CNS lymphoma (see notably Bonnan M, Ferrari S, Bertandeau E, Demasles S, Krim E, Miquel M, Barroso B. "*Intrathecal rituximab therapy in multiple sclerosis: review of evidence supporting the need for future trials. Cur Drug Targets*". 2014; 15(13):1205-14. Topping J, Dobson R, Lapin S, Maslyanskiy A, Kropshofer H, Leppert D, Giovannoni G, Evdoshenko E. "*The effects of intrathecal rituximab on biomarkers in multiple sclerosis*". Mult Scler Relat Disord. 2016 March; 6:49-53, and Kadoch C, Li J, Wong V S, Chen L, Cha S, Munster P, Lowell C A, Shuman M A, Rubenstein J L. "*Complement activation and intraventricular rituximab distribution in recurrent central nervous system lymphoma*". Clin Cancer Res. 2014 Feb. 15; 20(4): 1029-41).

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody directed against HERV-K Envelope protein (HERV-K Env) may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

Preferably, the antibody directed against HERV-K Envelope protein (HERV-K Env) of the invention can be formulated into a buffer in which it was solubilized, stored and injected to patients. Preferably, said buffer comprises 20 mM histidine, 5% sucrose, and 0.01% polysorbate 20 and present a pH of 6.0.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the patient being treated. The person responsible for administration will, in any event, determine the appropriate dose for the individual patient.

In addition to the compounds formulated for parenteral administration, such as intravenous, intrathecal or intramuscular injection, other pharmaceutically acceptable forms include, e.g. tablets or other solids for oral administration; time release capsules; and any other form currently used.

Diagnostic Methods of the Invention

In another aspect, the invention also relates to a method for detecting the HERV-K envelope protein in a biological sample comprising the step of contacting said biological sample with an anti-HERV-K envelope antibody as defined above.

In another aspect, the invention also relates to a method for diagnosing ALS in a patient comprising the step of contacting a biological sample obtained from said patient with an anti-HERV-K envelope antibody as defined above.

Typically, the biological sample can be a body fluid, such as cerebrospinal fluid.

Therapeutic Method and Monitoring Method According to the Invention

In one aspect, the invention also relates to a method for treating a patient suffering from ALS comprising administering to said patient an effective amount of an antibody that recognizes the HERV-K envelope protein as defined above.

Preferably, the patient is suffering from ALS, notably sporadic ALS.

Typically, said antibody is administered intrathecally, intravenously or subcutaneously.

The invention also relates to a method of treatment of a patient suffering from ALS, notably sporadic ALS, comprising the steps of:

1) predicting the prognosis of a patient by detecting and/or quantifying a HERV-K virus, in a biological sample; and then 2) if said step 1) shows the expression of a human endogenous retrovirus (HERV) type K, then the method of the invention comprises a step of providing the antibody of the invention to said patient.

The invention also relates to a method for monitoring the response to a treatment of a patient suffering from ALS, notably sporadic ALS, said method comprising the following steps:

a. treating said patient with the antibody according to the invention; then
b. detection and/or quantification of HERV-K in a biological sample of said patient.

According to the invention, in case of monitoring the response to a treatment of a patient suffering from ALS, a biological sample may be a sample of body fluids such as blood, cerebrospinal fluid, urine or in a disease-specific tissue biopsy.

Typically, the step of detection and/or quantification may be performed according to the routine techniques, well known of the person skilled in the art. Typically, said step comprises contacting a biological sample of the patient with selective reagents such as probes, primers, ligands or antibodies, and thereby detecting the presence of nucleic acids or proteins of interest originally in the sample.

In one embodiment, the detection and/or quantification step can be performed with the anti-HERV-K antibody as defined above.

FIGURE LEGENDS

FIG. 1: GN_mAb_Ev_K01 is an IgG2b murine antibody and has a kappa light chain. Isotyping was performed by ELISA on 1:10 diluted supernatant from GN_mAb_Env_K01 hybridoma (monoclonal stage) captured by anti-murine immunoglobulin. Detection with various anti-mouse light (A) or heavy (B) chains antibodies showed that GN_mAb_ENV_K01 is an IgG2b/kappa murine antibody. Results are plotted as $OD_{450nm}$ mean of duplicate values f SD.

FIG. 2: GN_mAb_Env_K01 light and heavy chains sequences RNA from hybridoma cells was extracted and reverse transcribed into cDNA that was amplified by PCR before sequencing with primers targeting cDNA encoding murine antibody heavy (A) and light (B) chains.

(A) CDR1 (Bold), CDR2 (underlined) and CDR3 (bold italics) sequences from kappa light chain;

(B) CDR4 (Bold), CDR5 (underlined) and CDR6 (bold italics) sequences from heavy chain; constant murine IgG2 Sequences (grey italics).

Figure 3:
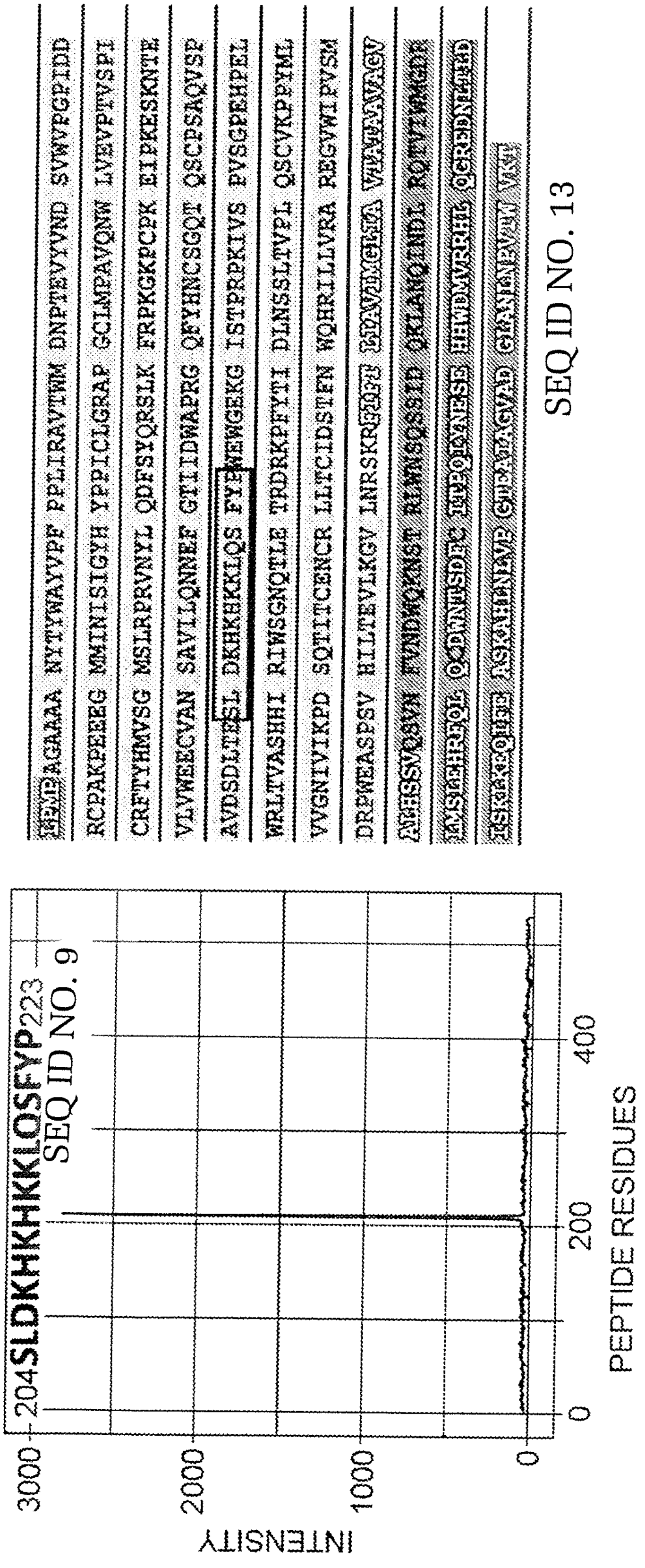

FIG. 3: GN_mAb_Env_K01 binds to HERV-K-Env SLDKHKHKKLQSFYP (SEQ ID NO: 9) epitope.

The intensity profile (left) of each peptide from HERV-K-Env (MyBiosource) (right) are displayed. These overlapping peptides of 15 amino acids with an offset of one residue showed that GN_mAb_Env_K01 binds to the linear SLDKHKHKKLQSFYP (SEQ ID NO:9) epitope. Results are presented as the intensity of signal (mAU) obtained on the CCD camera used, similar to a standard 96-well plate ELISA-reader.

Figure 4:
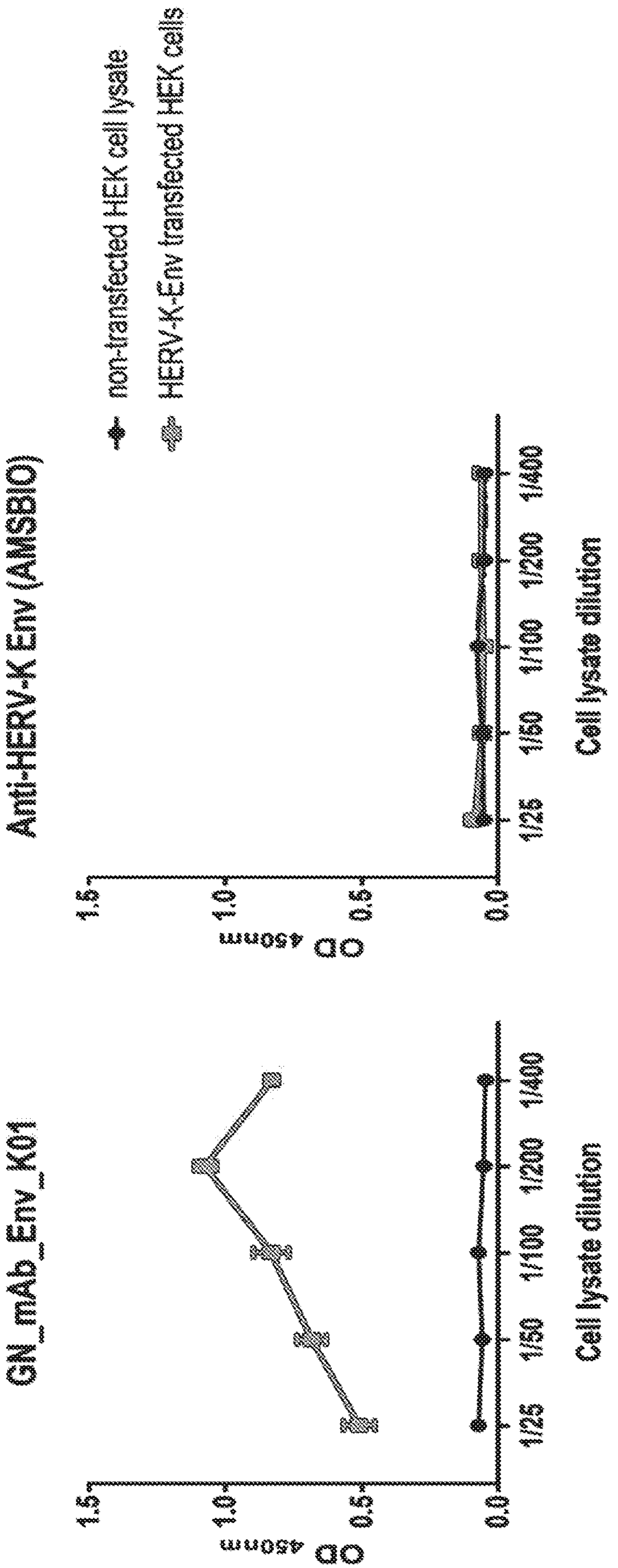

FIG. 4: Glycosylated HERV-K Env is detected by GN_mAb_ENV_K01 in ELISA.

GNmAb_Env_K01 (A) or Anti-HERV-K-Env from AMSBIO (B) (1 μg/ml) were used as primary antibodies in ELISA on HEK cell lysates at various dilutions (1:25, 1:50, 1:100, 1:200, 1:400). Contrary to Anti-HERV-K-Env (AMSBio) GN_mAb_Env_K01 recognized glycosylated HERV-K-Env. Results are plotted as $OD_{450nm}$ mean of duplicate values±SD.

Figure 5:
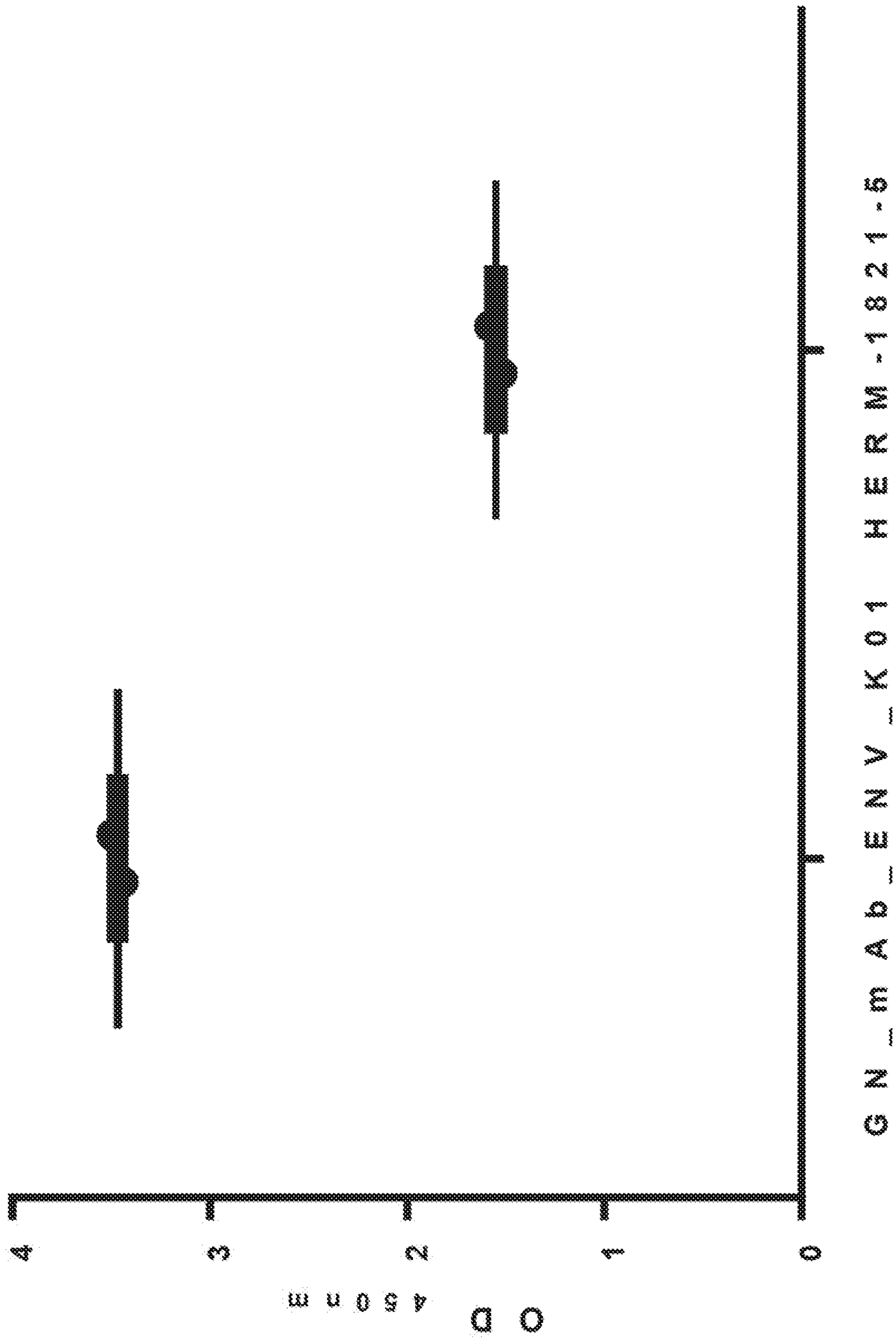

FIG. 5: Non-glycosylated HERV-K-Env is detected by GN_mAb_ENV_K01 in ELISA

GN_mAb_Env_K01 or Anti-HERV-K-Env from AMSBIO (ltg/ml) were used as primary antibodies in ELISA on 1 μg/ml of his-SUMO-HERV-K-Env recombinant protein from *E. Coli*. Both anti-HERV-K-Env recognized the non-glycosylated HERV-K-Env protein. Results are plotted as $OD_{450nm}$ mean of duplicate values±SD.

Figure 6:
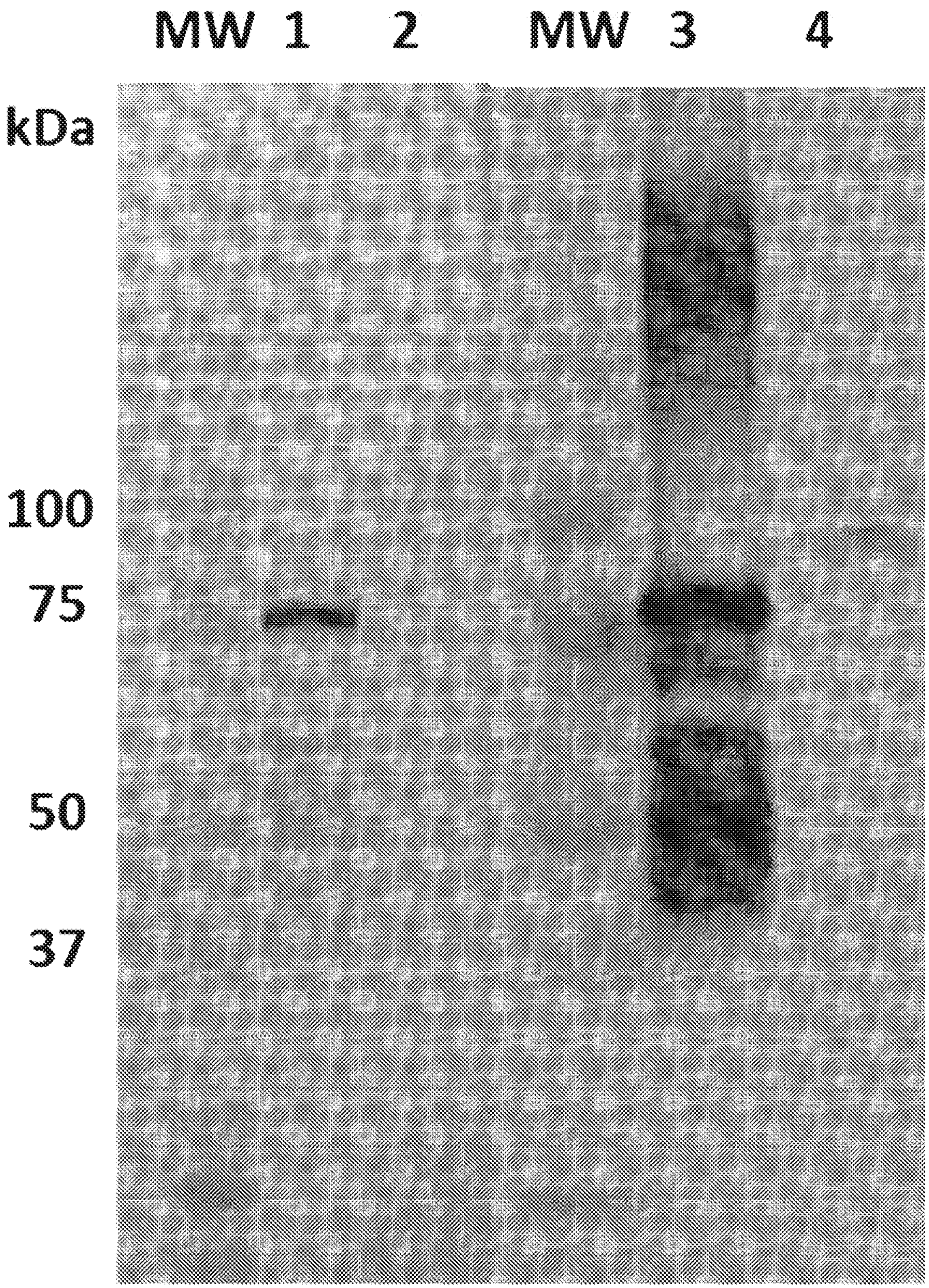

FIG. 6: HERV-K Env detection by Western Blotting with GN_mAB_ENV_K01

Anti-HERV-K-Env (ltg/ml) from AMSBIO (wells #1&2) or diluted (1:5) supernatant from GN_mAb_Env_K01 hybridoma (wells #3&4) were used as primary antibodies in western blotting. 0.2 μg of his-SUMO tagged HERV-K-Env were deposited in wells #1&3 and 24.5 μg of protein extract from HERV-K-Env transfected HEK cells were deposited in wells #2&4. Non-glycosylated his-SUMO tagged HERV-K-Env protein is detected at 75 kDa by both antibodies, along with multimers of high MW and cleaved fragments of lower MW. Glycosylated HERV-K-Env (90 kDa) is only detected with GN_mAb_Env_K01.

MW: molecular weight.

Figure 7:
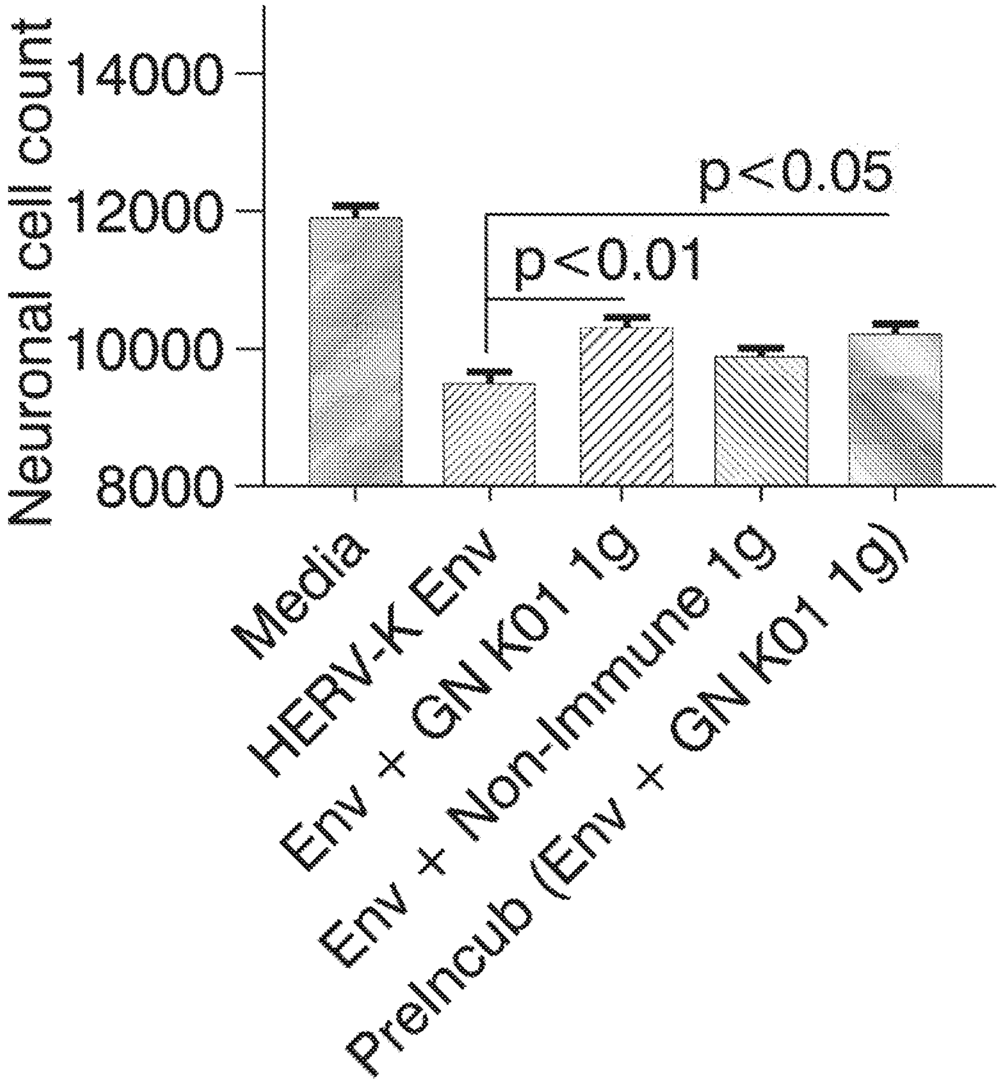

FIG. 7: GN_mAb_Env_K01 (GN K01) antibody specifically protects human neuronal cells from cytotolicity induced by extracellular HERV-K envelope protein: Cell survival assay.

Neuronal cultures were treated with differentiation media (see example 2) and with IgG samples GN K01 or control non-Immune IgG (Thermo Product # MA 1-10418) at a final concentration of 3 ug/mL. After 60 minute pre-incubation, recombinant HERV-K Env protein (My BioSource, amino acid 90-632, Cat # MBS1391552) was added to a final concentration of 100 nM. One sample of GN K01 Ig was pre-incubated with HERV-K Env for 30 minutes, and then added together to the human neurons. The neuronal cultures were observed with a GE INCell Analyzer 2000 BioImager to acquire images of each well (4 images per well) at various time points, in this experiment 5 days post Env treatment. The neuronal cell count was determined with GE Investigator high content imaging software. Arrow on top of histogram bar is showing the results with GN_mAb_Env_K01 (GN K01) antibody.

Figure 8:
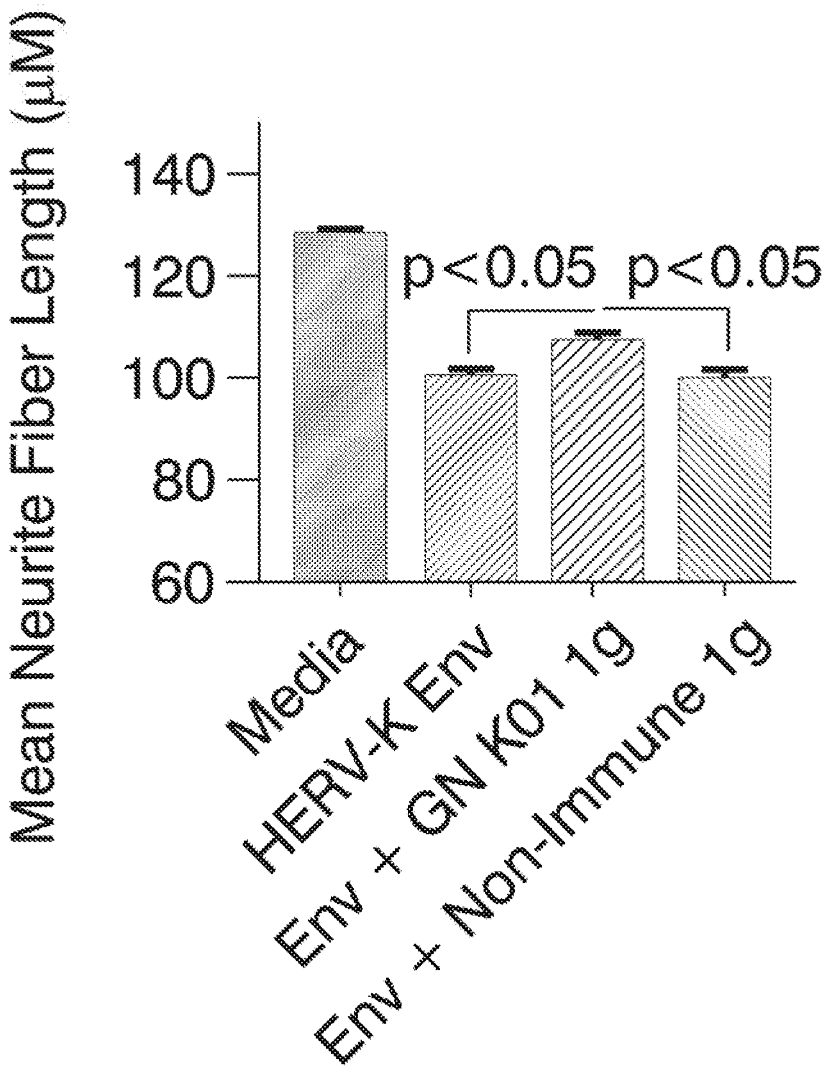

FIG. 8: GN_mAb_Env_K01 (GN K01) antibody specifically protects human neuronal cells from cytotoxicity induced by extracellular HERV-K envelope protein: neurite length.

Neuronal cultures were treated with differentiation media (described above) and with IgG samples GN K01 or control non-Immune IgG (Thermo Product # MA 1-10418) at a final concentration of 3 ug/mL. After 60 minute pre-incubation, recombinant HERV-K Env protein (My BioSource, amino acid 90-632, Cat # MBS1391552) was added to a final concentration of 100 nM. The neuronal cultures were observed with a GE INCell Analyzer 2000 BioImager to acquire images of each well (4 images per well) at various time points, in this experiment at 5 days post Env post treatment. The mean neurite fiber length was determined with GE Investigator high content imaging software.

Figure 9:
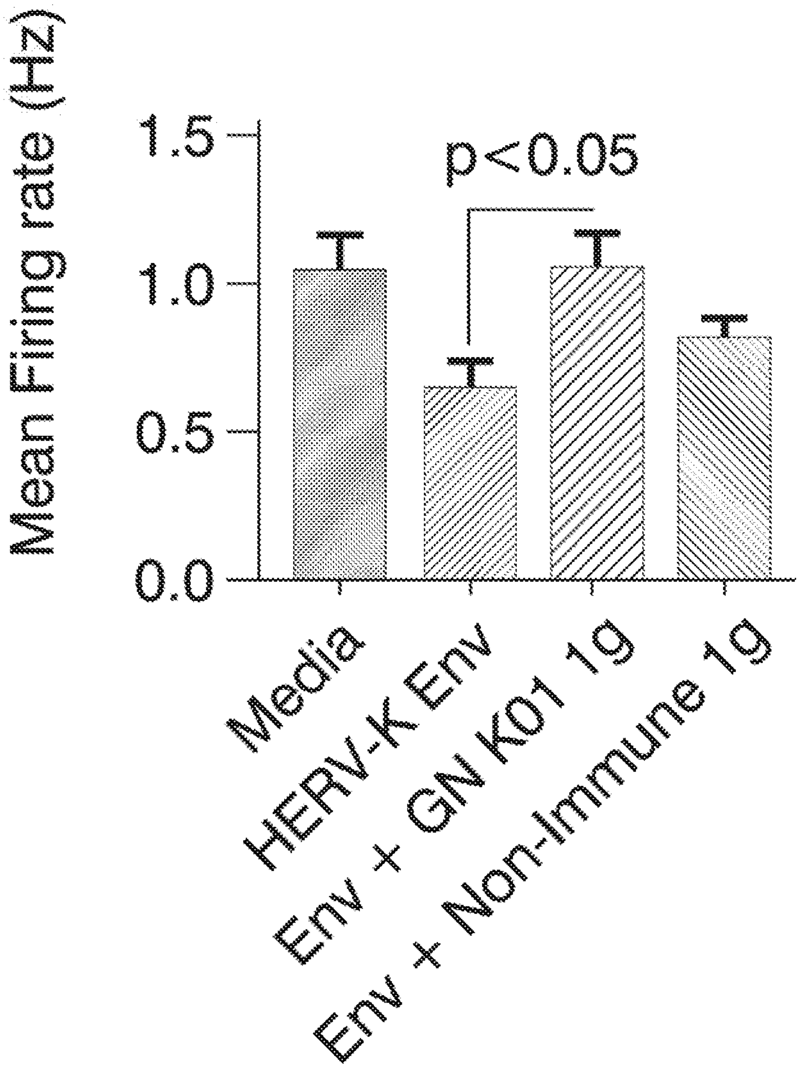

FIG. 9: GN_mAb_Env_K01 (GN K01) antibody specifically protects human neuronal cells from cytotoxicity induced by extracellular HERV-K envelope protein: neuron global electrophysiological activity.

Electrophysiological activity, noted by increased spike rate in the wells, increased significantly by 21 days in vitro and was monitored by recording spontaneous electrical activity in all wells for 5 minutes per day. At this point, the human neuronal cultures were treated with differentiation media (described above) and with GN K01 or control non-Immune IgG (Thermo Product # MA 1-10418) at a final concentration of 3 ug/mL. After 60 minute pre-incubation, recombinant HERV-K Env protein (My BioSource) was added to a final concentration of 100 nM. Spontaneous electrical activity was recorded daily afterward, beginning at 24 h post treatment. The mean firing rate was determined for each treatment group at 24 h post HERV-K Env exposure.

Arrow on top of histogram bar is showing the results with GN_mAb_Env_K01 (GN K01) antibody. Arrow on top of histogram bar is showing the results with GN_mAb_Env_K01 (GN K01) antibody.

EXAMPLES

Example 1: Development and Characterization of the GN_mAb_Env_K01 Antibody

1. Materials and Methods 1.1. Monoclonal Antibody Development 1.1.1. Immunization and Immune Cells Recovery Three female OF mice (Charles River) were immunized with his-SUMO tagged HERV-K-Env protein (75 kDa) from *E. coli* provided by Mybiosource (MBS1391552) following the confidential RAD (Rapid Antibody development) protocol from Biotem company.

Briefly, at day+10 (D+10) blood sample from immunized mice were analyzed by direct ELISA on the recombinant HERV-K Env protein (MyBiosource, MBS1391552) or *Escherichia coli* lysate as negative control. At D+13, immunized mice were sacrificed and immune cells from lymph nodes were collected and washed thrice with 45 ml of Dulbecco's Modified Eagle's medium (DMEM, SIGMA, D5671) following centrifugation at 244 g for 7 minutes and resuspension in 20 ml DMEM (SIGMA, D5671). Immune cells from immunized mice ($420\times10^6$ cells) were mixed with myeloma cells ($107\times10^6$ cells) in the exponential phase of growth according to a 1:3.9 ratio. Cells were centrifuged at 244 g for 7 minutes and the pellet was resuspended in 1 ml of the Polyethylene glycol (PEG) used as fusing agent (SIGMA, P7181). After the washing step including a centrifugation at 108 g for 12 minutes cells were resuspended in 10 ml of DMEM (SIGMA, D5671), 1× Hypoxanthine Aminopterine Thymidine (HAT, SIGMA, H0262-10VL), 20% foetal calf serum (FCS, PAA, A15-251), 4 mM L-Glutamine (SIGMA, G7513) and centrifuged at 244 g for 7 minutes. Cells were resuspended DMEM (SIGMA, D5671), 1×HAT (SIGMA, H0262-10VL), 20% FCS (PAA, A 15-251), 4 mM L-Glutamine (SIGMA, G7513) and stored for 2 hours at room temperature.

1.1.2. Fusion

At D-1, immunodeficient Nude mice (BIOTEM) were injected with 5 ml of DMEM (SIGMA, 05671) containing 20% FCS (PAA, A15-251) and 2+/−1 minutes later, macrophages from peritoneal fluid have been collected and cultivated in DMEM medium (SIGMA, D5671).

BALB/c spleen cells from mouse immunized with sheep red blood cells fused with P3X63Ag8 myeloma have already been selected, characterized and stored by BIOTEM. At D-10, these myeloma have been thawed and cultivated in DMEM (SIGMA, D5671)-8-Azaguanine (AZA, SIGMA, A5284)-10% FCS (PAA, A15-251).

Macrophages from Nude mice were counted and resuspended at $10^4$ macrophages/ml in DMEM (SIGMA, D5671), 1×HAT (SIGMA, H0262-10VL), 20% FCS (PAA, A15-251), 4 mM L-Glutamine (SIGMA, G7513), 1% penicillin/streptomycine (SIGMA, P0781). Then, 50 μl of macrophage suspension (corresponding to 500 macrophages) used as a growth factor has been plated in 96-wells plates with 50 μl of hybridomas cells suspension. These cells were cultivated at 37° C., 5% $CO_2$ for 21 days.

1.1.3. Cloning

Hybridoma cells were thawed and cultivated with DMEM (SIGMA. D5671), HT (hypoxantine 100 μM, thymidine 16 μM-SIGMA H0137), 20/FCS (PAA, A15-251), 2% Hybridoma Enhancing Supplement (HES, SIGMA, H6020), 4 mM L-Glutamine (SIGMA, G7513), 1% penicillin/streptomycine (SIGMA, P0781) in 24-wells plate during 1 week at 37° C., 5% C02. The day before cloning, hybridoma cells were split.

At D0, after serial dilutions at $10^4$, 50, 25, 5 and 2.5 cells/ml in culture medium hybridoma suspension were plated at 5, 1 and 0.5 cells/200 μl into the wells of a 96-wells plate. At D+6, 100 μl of supernatant from cell containing wells (selected through a screening with an optical microscope) was replaced by fresh DMEM (SIGMA, D5671), HT (hypoxantine 100 μM, thymidine 16 μM-SIGMA H0137), 20% FCS (PAA, A15-251), 2% HES (SIGMA, H6020), 1% penicillin/streptomycine (SIGMA, P0781).

After the first ELISA screening corresponding to D+10, anti-HERV-K-Env positive hybridoma were cultivated in 24-wells plates (0.5 ml/well).

After the second ELISA screening corresponding to D1)4, anti-HERV-K Env positive hybridoma were cultivated in plates or culture flask (Corning) and 5 vials containing 4 at $5\times10^6$ cells were frozen at −196° C. (liquid azote) in DMEM (SIGMA, D5671), 15% FCS (PAA, A15-251), 4 mM L-Glutamine (SIGMA, G7513), 1% HES (SIGMA, H6020), 1% penicillin/streptomycine (SIGMA, P0781), 20% Diméthylsulfoxyde (DMSO, Sigma, D2650) media.

1.2. Anti-HERV-K-Env ELISA

The maxisorp 96 conical bottom well plates (NUNC, 449824) were coated with 50 μl of 1 μg/ml HERV-K Env protein (Mybiosource, MBS1391552), *E. Coli* lysate (XL1-Blue MRF, Stratagene), HEK cell lysate in 1× Phosphate Buffered Saline (PBS, BIOTEM) overnight at room temperature. Plates were washed with [1×PBS+0.05% Tween20 (VWR, 28829.296)] washing buffer (300 μl/well). Non-specific binding sites were blocked with [1×PBS+0.05% Tween20+2.5% milk (Regilait)] blocking buffer (150 μl/well) for one hour at room temperature. Plates were washed with [1×PBS+0.05% Tween20] washing buffer (300 μl/well).

Antibody samples have been diluted in [1×PBS+0.05% Tween20+0.5% BSA (VWR, 1.12018.0100) dilution buffer. Antibody samples or purified anti-HERV-K-Env from AMS-BIO (1 μg/ml) (50 μl/well) were incubated for two hours at room temperature. The plates have been washed thrice with [1×PBS+0.05% Tween20] washing buffer (300 μL/well) and were incubated with 50 μl/well of polyclonal Peroxidase-conjugated affiniPure F(ab)'2 fragment Goat anti-mouse IgG+IgM (Jackson, 115-036-068) (1/10000 in 1×PBS+0.05% Tween20+0.5% BSA) for one hour at room temperature. Plates were washed thrice and the revelation was performed with Tetramethybenzidine (TMB, Eurobio, 52-00-01) substrate solution (50 μl/well) for 10 minutes at room temperature. The reaction was blocked with 0.1 M H2SO4 (Merck, 1.12080.1000) (50 μl/well). Optical density (OD) was measured at 450 nm using the optical density (OD) reader (Dynex).

13. Production, Purification, Dialysis

GN_mAb_Env_K01 hybridoma cells were thawed and cultivated first in T75 $cm^2$ and then in T300 $cm^2$ tissue culture flasks (Corning). Finally, 10 at $12\times10^6$ cells were cultivated in 500 ml of DMEM (SIGMA, D5671), 15% FCS (PAA, A15-251), 4 mM L-Glutamine (SIGMA, G7513), 1% HES (SIGMA H6020), 1% penicillin/streptomycine (SIGMA, P0781) medium in Hyperflask (Corning, 10030) at 37° C., 5% CO2 within 10+/−1 days.

The culture supernatant were centrifuged at 244 g for 7 minutes and filtered through a 11 μm nylon net filter (SIGMA, NY1104700) Protein A chromatography column (GE Healthcare, Mab Select Xtra) were washed twice with demineralized water and equilibrated with 5 volumes of 1×PBS (Biotem). Then 0.5 L of culture supernatant free of cells was loaded. The column was washed with 5 volumes of 1×PBS. Immunoglobulin elution was performed at acid pH with 3.5+/−0.5 volumes of acetic acid (SIGMA, A6283). Eluted fractions containing immunoglobulins were neutralized with 100 μl of 1M Tris pH 8.8 buffer (Biotem) and stored at 4° C.

IgG purified fractions were dialyzed twice on 0.5 ml micro dialysis capsule Quixsep® (Roth, H448-1) with 10 kDa SnakeSkin Dialysis Tubing, 22 mm (Thermofischer, 68100) for 2 hours in 1×PBS at 4° C. and concentrated by centrifugation at 4° C. on Vivaspin 20 (30 Kda) (Sartorius, ref). Antibodies were filtered on 0.22 μm Minisart® filter (Sartorius, ref) and the protein concentration was measured by spectrophotometry at 280 nm.

1.4. Purity Analysis by SDS PAGE Gel Electrophoresis

Antibody (5 μl at 0.2 μg/μl) previously diluted in Laemmli buffer (Biotem) were heated for 5 minutes at 95° C. and separated on a 13.5% sodium dodecyl sulfate-polyacrylamide gel electrophoresis (SDS-PAGE) containing a stacking gel with 5% SDS-PAGE. Gel was run for 30 minutes at 90V and then at 120V for 2 hours. Protein detection was done using colorizing solution (Biotem) for 1 hour with agitation. The gel was washed with decolorizing solution (Biotem) for 1 hour with agitation.

1.5. Isotyping 1.5.1. Isotyping by ELISA

The maxisorp 96 conical bottom well plates (NUNC, 449824) was coated with 50 μl of 1 μg/ml anti-murine Immunoglobulin (Clinisciences, 1010-01) overnight at room temperature. Plates were washed with [1×PBS+0.05% Tween20] washing buffer (300 μl/well). Non-specific binding sites were blocked with [1×PBS+0.05% Tween20+2.5% milk] blocking buffer (150 μl/well) for one hour at room temperature. Plates were washed with [1×PBS+0.05% Tween20] washing buffer (300 μl/well). Hybridoma supernatant was 1:10 diluted in [1×PBS+0.05% Tween20+0.5% BSA] dilution buffer. Sample (50 μl/well) was incubated for two hours at room temperature. The plates were washed once with [1×PBS+0.05% Tween20] washing buffer (300 μl/well) and were incubated with 50 μl/well of peroxidase conjugated goat anti-mouse heavy chain (IgA, IgG1, IgG2a, IgG2b, IgG3, IgM) (Clinisciences, 5300-05) (1/2000 in 1×PBS+0.05% Tween20+0.5% BSA) for one hour at room temperature. Plates were washed once and the revelation was performed with TMB (Eurobio, 52-00-01) substrate solution (50 μl/well) for 10 minutes at room temperature. The reaction was blocked with 0.1M $H_2SO_4$ (Merck, 1.12080.1000) stop solution (50 μl/well). Optical density (OD) was measured at 450 nm using the optical density (OD) reader (Dynex).

1.5.2. Isotyping by Lateral-Flow Immunoassay

Light chain (kappa or lambda) were characterized with a lateral-flow immunoassay (LFIA) (ThermoFisher, 26179).

1.6. HEK Transfection

Human embryonic cells ($1.10^6$ cells/mL) were transfected with 1 μg of HERV-K-Env (accession number AY037928.1) expressing plasmid. Transfected cells were cultivated at 37° C., 8% $CO_2$, 120 rpm agitation.

1.7. Western Blot Analysis

The recombinant HERV-K-Env protein (Mybiosource) at 12.5 ng/μl and the protein lysate from HEK transfected cells at 1.5 μg/μl were diluted (1:1) in 2× Laemmli buffer (SIGMA, S3401) and heated for 5 minutes at 90° C. Then, 32 μl of samples were loaded on a 8-16% sodium dodecyl sulfate-polyacrylamide gel electrophoresis (SDS-PAGE, Novex, EC60452BOX). Gels were run for 1 hour at 160 mA in 1× Tris-Glycine SDS running buffer (Novex, LC2675). After the protein transfer onto a 0.2 μm nitrocellulose membrane (Biorad, 162-0146) in 1× Tris-Glycine transfer buffer (Novex, LC3675), the membrane was blocked for 1 hour with [1×PBS+5% milk (La Vie Claire)] blocking buffer on a rotating platform at room temperature. Cell supernatant from GN_mAb_Env_K01 hybridoma was 1:5 diluted in [1×PBS+1% milk] antibody diluent and used as primary antibody by incubation for 1 hour. The membrane was then washed thrice for 5 minutes in [1×PBS+0.05% Tween20

(SIGMA, P7949)] washing buffer and incubated for 30 minutes with 1:1000 diluted HRP-conjugated goat anti-mouse IgG antibody (Jackson, 115035-146). Membrane was washed thrice and protein of interest was detected with a colorometric reaction (Opti 4-CN, Biorad, 170-8235), according to the provided protocol.

1.8. Epitope Mapping

Epitope mapping was conducted at Pepscan Presto BV, (Zuidersluisweg 2, 8243RC Lelystad, The Netherlands).

1.8.1. Peptides Library Synthesis

To reconstruct epitopes of the target molecule a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was done using Pepscan's proprietary Chemically Linked Peptides on Scaffolds (CLIPS) technology. CLIPS technology allows to structure peptides into single loops, doubleloops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis(bromomethyl)pyridine) is dissolved in ammonium bicarbonate (20 mM, pH 7.8)/acetonitrile (1:3(v/v)). This solution is added onto the peptide arrays. The CLIPS template will bind to side-chains of two cysteines as present in the solid-phase bound peptides of the peptide-arrays (455 wells plate with 3 μl wells). The peptide arrays are gently shaken in the solution for 30 to 60 minutes while completely covered in solution. Finally, the peptide arrays are washed extensively with excess of H2O and sonicated in disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

1.8.2. ELISA Screening

The binding of antibody to each of the synthesized peptides was tested in a Pepscan-based ELISA. The peptide arrays were incubated with primary antibody solution (GN-_mAb_Env_K01 at 1 μg/ml in Pepscan Buffer) overnight at 4CC. After washing, the peptide arrays were incubated with a 1/1000 dilution of a rabbit anti-mouse IgG(H+L) HRP conjugate antibody (Southern Biotech; Table 4) for one hour at 25° C. After washing, the peroxidase substrate 2,2'-azino-di-3-ethylbenzthiazoline sulfonate (ABTS) and 20 μl/ml of 3 percent H2O2 were added. After one hour, the color development was measured. The color development was quantified with a charge coupled device (CCD)-camera and an image processing system. The values obtained from the CCD camera range from 0 to 3000 mAU, similar to a standard 96-well plate ELISA-reader.

1.9. Sequencing

High quality RNA was extracted and purified from hybridoma cells using PureLink RNA Mini Kit (Life technologies, 12183018A) and controlled on agarose gel. Starting from purified total RNA, Superscript enzyme (Invitrogen, 18064022) was then used to synthesize first-strand complementary DNA (cDNA) followed by a Polymerase chain reaction (PCR) using HotStar HiFidelity Polymerase Kit (Qiagen, 202602) and degenerate primers (Biotem design) targeting specifically cDNA encoding for murine antibody heavy and light chains. PCR products were controlled on agarose gel and sequenced (double strand sequencing). The resulting sequences were analyzed for assembling and quality controls using dedicated to bioinformatics tools (Blast-ClustalW) and translated to peptidic sequences.

1.10. Biotem Buffer Composition

TABLE 1

| BIOTEM Buffer composition | |
|---|---|
| Solution | Composition |
| 10 × PBS | 80 g NaCl<br>2 g KCl<br>28.7 g Na2HPO4—12H2O<br>2.4 g KH2PO4 into 1 L of deionized water |
| 1 × PBS | 100 ml 10× PBS<br>900 ml deionized water |
| Laemmli buffer (4×) | 0.5 ml of 2.5M Tris pH 6.8 (ICN, 103133)<br>0.6 g of 12% Sodium Dodecyl Sulfate (ICN, 102918)<br>0.01 g of 0.2% Bleu de Bromophénol<br>2 ml of 40% Glycerol (SIGMA, G7757)<br>qsp 5 ml H2O<br>(reducing conditions: 1 ml of 20% 2-Mercaptoéthanol (SIGMA, M7154) |
| 13.5% Separating SDS-PAGE | 9 ml of 30% acrylamide (SIGMA, A3699)<br>5 ml of 1.5M Tris pH 8.8 (ICN, 103133)<br>200 μl of 10% Sodium Dodecyl Sulfate (ICN, 102918)<br>5.8 ml $H_20$<br>105 μl Ammonium persulfate (APS, ICN, 802811)<br>15 μl TEMED (ICN, 805615) |
| 5% stacking SDS-PAGE | 1.6 ml of 30% acrylamide (SIGMA, A3699)<br>2.5 ml of 0.5M tris pH 6.8 (ICN, 103133)<br>100 μl of 10% Sodium Dodecyl Sulfate (ICN, 102918)<br>5.8 ml $H_20$<br>150 μl Ammonium persulfate (APS, ICN, 802811)<br>15 μl TEMED (ICN, 805615) |
| 10× Running buffer | 288 g Glycine (SIGMA, G7126)<br>60 g Tris base (ICN, 103133)<br>20 ml SDS (ICN, 102918)<br>qsp 2 L $H_20$ |
| colorating solution | 45 ml acetic acid (Sigma, A6283)<br>278 ml ethanol 90%<br>177 ml $H_2O$<br>0.75 g Brillant blue Reagent (SIGMA, B7920) |
| decolorating solution | 75 ml acetic acid (SIGMA, A6283)<br>56 ml éthanol 90%<br>869 ml $H_2O$ |

2. Results

Using specific anti-immunoglobulin antibodies that are capable of detecting the different heavy and light chains of monoclonal antibodies we have shown that GN_mAb_Env_K01 was detected by anti-Kappa light chain antibodies (FIG. 1A) and anti-IgG2b heavy chain (FIG. 1B).

GN_mAb_Env_K01 heavy and light chains were sequenced, showing their three CDR regions (FIG. 2) and confirming both IgG2b heavy and kappa light chains.

2.1. GN_mAb_Env_K01 Recognizes the Linear Epitope SLDKHKHKKLQSFYP from HERV-K-Env Surface Unit.

Using a panel of 529 peptides among the sequence of truncated HERV-K-Env protein from Mybiosource (no signal peptide and truncated transmembrane domain) epitope mapping test under high stringency conditions reveals that GN-mAb-Env_K01 antibody bound to linear peptide with SLDKHKHKKLQSFYP core sequence (FIG. 3, left panel). This epitope is contained within the extracellular domain of HERV-K-Env protein (FIG. 3 right panel), corresponding to the 298-312 region of the HERV-K-Env protein described by Dewannieux et al (Dewannieux, Blaise, and Heidmann 2005). Blasting this epitope into Blastp from the National Center for Biotechnology Information (NCBI) reveals that it is a highly conserved epitope with 100% homology within the top 100 blast hits corresponding to HERV-K-Env sequences (data not shown).

2.2. GN_mAb_Env_K01 Recognizes Glycosylated and Non-Glycoylated HERV-K-Env Proteins in Native Conditions.

We have further analyzed the ability of GN_mAb_Env_K01 to recognize glycosylated HERV-K-Env. For this purpose, human embryonic kidney (HEK) cells were transfected with a plasmid encoding HERV-K-Env protein. Despite several attempts with various buffers, we failed to extract soluble HERV-K-Env protein (data not shown). However this insoluble fraction of glycosylated HERV-K-Env protein from transfected HEK cell lysate could show that GN_mAb_Env_K01 specifically recognizes the glycosylated HERV-K-Env antigen by ELISA (FIG. 4, left panel). Conversely, the classical commercial anti-HERV-K-Env mAb (HERM-1821-5, IgG2b) from AMSBIO (FIG. 4, right panel) did not detect the glycosylated HERV-K-Env.

The present results indicate that GN_mAb_Env_K01 is biologically active in ELISA and confirm that SLDKHKHKKLQSFYP (SEQ ID NO: 9) epitope is accessible in native conditions.

Though both GN_mAb_Env_K01 and Anti-HERV-K-Env mAb (HERM-1821-5, IgG2b) from AMSBIO recognized native his-SUMO tagged recombinant HERV-K-Env from *E. Coli* (FIG. 5), it appeared that GN_mAb_Env_K01 gave a much higher detection compared to Anti-HERV-K-Env mAb counterpart from AMSBIO (FIG. 5) when both are tested at the same concentration (1 μg/ml). This evidences a higher affinity of GN_mAb_Env_K01 for HERV-K Env.

As shown in FIG. 6, both GN_mAb_Env_K01 and Anti-HERV-K-Env mAb (HERM-1821-5, IgG2b) from AMSBIO recognized denatured his-SUMO tagged recombinant HERV-K-Env from *E. Coli* as observed with the 75 kDa signal.

Importantly, GN_mAb_Env_K01 also detects denatured HERV-K-Env glycosylated proteins from HEK transfected cells as observed with the signal at 90 kDa, while no signal was detected with anti-HERV-K-Env antibody from AMSBIO. In addition to previous ELISA results with non-denatured proteins, GN_mAb_Env_K01 is biologically active in Western blot. The SLDKHKHKKLQSFYP (SEQ ID NO: 9) epitope is therefore also accessible in denaturing conditions.

4. Conclusions

The present report reveals that, after mouse immunization, antibody screening and monoclonal hybridoma selection, a murine monoclonal antibody (named GN_mAb_EnvK-01) recognizing HERV-K-Env SLDKHKHKKLQSFYP epitope has been developed and has been revealed to display unexpected properties.

Biological comparison with another anti-HERV-K Env mAb (HERM-1821-5, IgG2b) from AMSBIO confirms that, despite their similar origin (murine), isotype (IgG2b, kappa) and protein target (HERV-W-Env protein), GN_mAb_EnvK-01 is advantageous since recognizing both glycosylated and non-glycosylated proteins, while displaying high affinity in both native and denaturing conditions. In addition, the GN_mAb_EnvK-01 antibody targets a stable and conserved epitope among HERV-K envelope sequences from numerous and various copies described in the databases.

GN_mAb_EnvK-01 is therefore a useful tool, not only for immunoassays, but also for therapeutic purpose against HERV-K Env proteins as therapeutic targets in, e.g. ALS. Its stable epitope sequence among HERV-K copies, its high affinity and its efficient binding to native glycosylated forms, fulfill important requirements for a valuable therapeutic in patients with, e.g. ALS in which different HERV-K copies seem to be significantly expressed.

Example 2: GN_mAb_Env_K01 (GN K01) Antibody Efficiently Neutralizes HERV-K Envelope Neurotoxicity to Human Neuronal Cells 1. Materials and Methods 1.1. Human Neuronal Cells Human neural stem cell (NSC)-derived neuronal cultures were prepared as described (Efthymiou, Shaltouki et al. 2014). Briefly, NSCs were split into a 96-well plate coated with 0.002% poly-L-omithine (Sigma, St. Louis, Mo.) and 10 μg/mL laminin (Life Technologies) at 7500 to 10,000 cells/cm2, and neuronal differentiation medium was added 24 h after plating. The differentiation medium contained DMEM/F12 with GlutaMax, 1.8% bovine serum albumin (BSA), 1× StemPro hESC supplement (all from Life Technologies), 10 ng/mL brain-derived neurotrophic factor (BDNF) and glial cell line-derived neurotrophic factor (GDNF; R&D Systems, Minneapolis, Minn.), and cells received fresh medium and growth factors every other day. Neurons day 7-12 in vitro were utilized in neurotoxicity assays.

1.2 Neurotoxicity Assays:

1.2.1. Neuronal Morphology and Viability

Human neuronal cultures (15-20,000 cells per well), stably expressing Td-Tomato fluorescent protein to label the cells and processes, were plated onto 96 well plates as described above and were maintained at 37° C. in a humidified tissue culture incubator at 5% CO2. Neuronal cultures were treated with differentiation media (described above) and with IgG samples GN K01 or control non-Immune IgG (Thermo Product # MA 1-10418) at a final concentration of 3 ug/mL. After 60 minute pre-incubation, recombinant HERV-K Env protein (My BioSource, amino acid 90-632, Cat # MBS1391552) was added to a final concentration of 100 nM. One sample of GN K01 Ig was pre-incubated with HERV-K Env for 30 minutes, and then added together to the human neurons. The neuronal cultures were observed with a GE INCell Analyzer 2000 BioImager to acquire images of each well (4 images per well) at various time points, 24, 48, 72 h post treatment. High content imaging/analysis of these cultures was achieved with GE Investigator 1.93 analysis software. Neuronal viability, neurite length and other morphological parameters were quantitated for each sample. The data were depicted with Graph Pad Prism 7.02.

1.2.2 Electrophysiological Analysis

Electrophysiological analysis with Axion Maestro microelectrode array (MEA) assays.

48-well t-MEA plates were utilized to plate the human neuronal cultures for analysis. These plates contain 16 active recording electrodes per well. 200,000 neurons were applied to each well of the t-MEA plate and cultures were maintained at 37° C. in a humidified tissue culture incubator at 5% $CO_2$. Electrophysiological activity, noted by increased spike rate in the wells, increased significantly by 21 days in vitro and was monitored by recording spontaneous electrical activity in all wells for 5 minutes per day. At this point, the human neuronal cultures were treated with differentiation media (described above) and with IgG samples GN K01 or control non-Immune IgG (Thermo Product # MA 1-10418) at a final concentration of 3 ug/mL. After 60 minute pre-incubation, recombinant HERV-K Env protein (My Bio-Source) was added to a final concentration of 100 nM. In these conditions, the antibody is first added to the cells without Env., thus reproducing the conditions of a treated patients with presence of therapeutic antibody that diffused in his brain tissue. Thereafter the active Env protein (not-pre-incubated with the antibody, not "pre-neutralized and not added as an inactive protein) is added, thereby reproducing the expression of the pathogenic protein with an extracellular secretion in the extracellular space. One sample of GN K01 Ig was pre-incubated with HERV-K Env for 30 minutes, and then added together to the human neurons. Spontaneous electrical activity was recorded daily afterward, beginning at 24 h post treatment. Quantitation of electrical activity was completed with Axion Axis software. Parameters such as number of spikes, mean firing rate and number of bursts were determined for each treatment.

2. Results 2.1. Extracellular HERV-K Envelope Protein is Toxic to Human Neuronal Cells and its Toxicity is Specifically Inhibited by GN_mAb_Env_K01 (GN K01) Antibody 2.1.1. Neuronal Viability Human neuronal cultures treated with 100 nM recombinant HERV-K Env protein displayed significant neurotoxicity, resulting in important neuronal cell loss within next days. The effects of HERV-K Env were quantitated at 5 days after exposure to HERV-K Env protein. We observed that the Env+GN K01 Ig (3 μg/mL) treated neurons had increased survival compared to Env treated neurons. When analyzed five days after the HERV-K envelope protein was added to the culture medium, cells treated with Env plus 3 μg/mL of non-immune IgG control antibody exhibited similar toxicity. Neurons treated with GN K01 3 μg/mL, either prior to HERV-K Env or pre-incubated with Env and then applied to the neuronal cultures showed significantly more viable neurons, thereby confirming the efficacy of GN K01 antibody in neutralizing the toxicity of HERV-K Env protein (FIG. 7).

2.1.2. Neuronal Neurite Length

The effect of HERV-K Env on mean neurite length was analyzed in parallel, and addition of GN K01 (3 μg/mL) to Env exposed neurons significantly increased neurite length compared to Env or Env+control non-Immune Ig treated neurons (FIG. 8).

2.1.3. Neuronal Functional Activity

Electrophysiological studies with the Axion Maestro MEA system were conducted to evaluate whether HERV-K Env treatment resulted in functional changes to spontaneous electrical activity, which is a major feature of normal neuronal activity. After plating the human neuronal cultures on the 48 well MEA plates for 21 days, the cultures were incubated in differentiation media (described above) and with GN K01 or control non-Immune IgG (Thermo Product # MA 1-10418) at a final concentration of 3 μg/mL. After 60 minute pre-incubation, recombinant HERV-K Env protein (My BioSource, Cat # MBS1391552) was added to a final concentration of 100 nM. One sample of GN K01 Ig was pre-incubated with HERV-K Env for 30 minutes, and then added together to the human neurons. Spontaneous electrical activity was recorded beginning at 24 h post treatment. 24 h post HERV-K Env treatment, the number of spikes and mean firing rate decreased by 40% with Env treatment. Neurons exposed to HERV-K Env plus control non-immune IgG treatment showed about 30% decrease in the number of spikes and mean firing rate. Most interestingly, neurons exposed to HERV-K Env plus GN K01 showed number of spikes and mean firing rates similar to the wells incubated with control media only, thereby showing complete inhibition of HERV-K Env pathogenic effects on global neuronal functional activity (FIG. 9).

3. Conclusions

The efficacy of GN K01 antibody was therefore specific and its beneficial effects against the pathogenic consequences of neuronal exposure to HERV_K Env protein were evidenced by its significant (i) inhibition of cell death, (ii) maintenance of neuron cell morphology and neurite length and (iii) full recovery of neuronal functional activity as measured by electrophysiological activity in the presence of pathogenic of HERV-K Env protein, versus same exposure to HERV-K Env with an irrelevant control antibody or without antibody.

Therefore, (i) after the specific detection of HERV-K Env protein in the altered neurons within the brain parenchyma of patients with sporadic ALS was shown and (ii) after the proof of concept that this HERV-K Env protein alone drives the pathogenicity has been brought by clinical and histological signs of sporadic ALS reproduced in transgenic mice expressing HERV-K env gene encoding this unique protein (Li, Lee et al. 2015), the specific efficacy of GN K01 antibody, as demonstrated by the inventors on relevant human neuron cellular and functional aspects, is evidencing its therapeutic value in ALS, in particular in sporadic ALS.

The specific activity of such an antibody appears to neutralize (i.e: treat) the pathogenic effects of the HERV-K envelope (Env) protein, which itself was shown to be associated with ALS pathognomonic neuronal lesions in the brain of patients with sporadic ALS and to reproduce the same neuronal alterations when added to cultured neurons, or when expressed as a single transgene in mice along with the same clinical signs as in ALS. Moreover, the addition of the GN K01 antibody in the presence of the HERV-K Env pathogenic protein shows more significant efficacy that pre-incubation of GN K01 with HERV-K Env recombinant protein in vitro, which shows its optimal efficacy in physiological conditions, therefore in a therapeutic application.

HERV_K protein toxicity not only involves intracellular expression in transfected target cells or in neurons from transgenic animals from previous knowledge, but also involves secreted extracellular HERV-K protein pathogenic to naive (non-HERV-K transfected or overexpressing) neurons. Therefore, an antibody of the invention also protects human neuronal cells from paracrine spreading of cytotoxicity induced by neuronal exposure to secreted and/or extracellular HERV_K Env protein. Implicitly, this also applies to autocrine cytotoxicity by HERV_K Env protein produced in neurons expressing or overexpressing HERV-K env coding gene(s).

As a conclusion, the antibody specifically targeting HERV-K envelope protein according to the invention can neutralize its pathophysiological properties as observed in ALS, notably in sporadic ALS, or in HERV-K env mouse transgenic models reproducing ALS features.

REFERENCES

Alfahad, T., and A. Nath. 2013. 'Retroviruses and amyotrophic lateral sclerosis', *Antiviral Res,* 99: 180-7.

Andrews, W. D., P. W. Tuke, A. Al-Chalabi, P. Gaudin, S. ljaz, M. J. Parton, and J. A. Garson. 2000. 'Detection of reverse transcriptase activity in the serum of patients with motor neurone disease', *J Med Virol,* 61: 527-32.

Buratti, E., and F. E. Baralle. 2009. 'The molecular links between TDP-43 dysfunction and neurodegeneration', *Adv Genet,* 66: 1-34.

Dewannieux, M., S. Blaise, and T. Heidmann. 2005. 'Identification of a functional envelope protein from the HERV-K family of human endogenous retroviruses', *J. Virol,* 79: 15573-7.

Douville, R., J. Liu, J. Rothstein, and A. Nath. 2011. 'Identification of active loci of a human endogenous retrovirus in neurons of patients with amyotrophic lateral sclerosis', *Ann Neurol,* 69: 141-51.

Douville, R. N., and A. Nath. 2014. 'Human endogenous retroviruses and the nervous system', *Handb Clin Neurol,* 123: 465-85.

Duperray. A., D. Barbe, G. Raguenez, B. B. Weksler, I. A. Romero, P. O. Couraud, H. Perron, and P. N. Marche. 2015. 'Inflammatory response of endothelial cells to a human endogenous retrovirus associated with multiple sclerosis is mediated by TLR4*', Int Immunol,* 27: 545-53.

Efthymiou, A., A. Shaltouki, J. P. Steiner, B. Jha, S. M. Heman-Ackah, A. Swistowski, X. Zeng, M. S. Rao and N. Malik (2014). "Functional screening assays with neurons generated from pluripotent stem cell-derived neural stem cells." J Biomol Screen 19(1): 32-43.

Geser, F., M. Martinez-Lage, L. K. Kwong, V. M. Lee, and J. Q. Trojanowski. 2009. 'Amyotrophic lateral sclerosis, frontotemporal dementia and beyond: the TDP-43 diseases', *J Neurol,* 256: 1205-14.

Hardiman, O., L. H. van den Berg, and M. C. Kiernan. 2011. 'Clinical diagnosis and management of amyotrophic lateral sclerosis', *Nat Rev Neurol,* 7: 639-49.

Lagier-Tourenne, C., and D. W. Cleveland. 2009. 'Rethinking ALS: the FUS about TDP-43*', Cell,* 136: 1001-4.

Li, W., M. H. Lee, L. Henderson, R. Tyagi, M. Bachani, J. Steiner, E. Campanac, D. A. Hoffman, G. von Geldern, K. Johnson, D. Maric, H. D. Morris, M. Lentz, K. Pak, A. Mammen, L. Ostrow, J. Rothstein, and A. Nath. 2015. 'Human endogenous retrovirus-K contributes to motor neuron disease', *Sci Tranl Med,* 7: 307ra153.

MacGowan, D. J., S. N. Scelsa, T. E. Imperato, K. N. Liu, P. Baron, and B. Polsky. 2007. 'A controlled study of reverse transcriptase in serum and CSF of HIV-negative patients with ALS', *Neurology,* 68: 1944-6.

Mallet, F., O. Bouton, S. Prudhomme, V. Cheynet, G. Oriol, B. Bonnaud, G. Lucotte, L. Duret, and B. Mandrand. 2004. 'The endogenous retroviral locus ERVWE1 is a bona fide gene involved in hominoid placental physiology', *Proc Natl Acad Sci USA,* 101: 1731-6.

Manghera, M., J. Ferguson-Parry, and R. N. Douville. 2016. 'TDP-43 regulates endogenous retrovirus-K viral protein accumulation', *Neurmbiol Dis,* 94: 226-36.

McCormick, A. L., R. H. Brown, Jr., M. E. Cudkowicz, A. Al-Chalabi, and J. A. Garson. 2008. 'Quantification of reverse transcriptase in ALS and elimination of a novel retroviral candidate', *Neurology,* 70: 278-83.

Moulignier, A., A. Moulonguet, G. Pialoux, and W. Rozenbaum. 2001. 'Reversible ALS-like disorder in HIV infection', *Neurolog.,* 57: 995-1001.

Oluwole, S. O., Y. Yao, S. Conradi, K. Kristensson, and H. Karlsson. 2007. 'Elevated levels of transcripts encoding a human retroviral envelope protein (syncytin) in muscles from patients with motor neuron disease', *Amytroph Lateral Scler,* 8: 67-72.

Perron, H., J. P. Perin, F. Rieger, and P. M. Alliel. 2000. 'Particle-associated retroviral RNA and tandem RGH/HERV-W copies on human chromosome 7q: possible components of a 'chain-reaction' triggered by infectious agents in multiple sclerosis?', *J Neurovirol,* 6 Suppl 2: S67-75.

Polymenidou, M., and D. W. Cleveland. 2011. 'The seeds of neurodegeneration: prion-like spreading in ALS', *Cell,* 147: 498-508.

Rolland, A., E. Jouvin-Marche, C. Viret, M. Faure, H. Perron, and P. N. Marche. 2006. The envelope protein of a human endogenous retrovirus-W family activates innate immunity through CD14, TLR4 and promotes Th1-like responses', *J Immunol,* 176: 7636-44.0

Rosen, D. R. 1993. 'Mutations in Cu/Zn superoxide dismutase gene are associated with familial amyotrophic lateral sclerosis', *Nature,* 364: 362.

Steele, A. J., A. Al-Chalabi, K. Ferrante, M. E. Cudkowicz, R. H. Brown, Jr., and J. A. Garson. 2005. 'Detection of serum reverse transcriptase activity in patients with ALS and unaffected blood relatives', *Neurology,* 64: 454-8.

Taylor, J. P., R. H. Brown, Jr., and D. W. Cleveland. 2016. 'Decoding ALS: from genes to mechanism', *Nature,* 539: 197-206.

Turner, G., M. Barbulescu, M. Su, M. I. Jensen-Seaman, K. K. Kidd, and J. Lenz. 2001. 'Insertional polymorphisms of full-length endogenous retroviruses in humans', *Curr Biol,* 11: 1531-5.

von Giesen, H. J., R. Kaiser, H. Koller, K. Wetzel, and G. Arendt. 2002. 'Reversible ALS-like disorder in HIV infection. An ALS-like syndrome with new HIV infection and complete response to antiretroviral therapy', *Neurology,* 59: 474; author reply 74-5.

Vucic, S., and M. C. Kiernan. 2009. 'Pathophysiology of neurodegeneration in familial amyotrophic lateral sclerosis', *Curr Mol Med,* 9: 255-72.

The invention claimed is:

1. A method of alleviating or inhibiting the progress of symptoms of sporadic amyotrophic lateral sclerosis (ALS) by neutralizing a HERV-K envelope protein in a subject in need thereof, comprising administering to the subject a therapeutically effective amount of the antibody that recognizes the HERV-K envelope protein, wherein said antibody comprises a light chain comprising a light chain variable region (VL) which comprises three complementarity determining regions (CDR-L1, CDR-L2 and CDR-L3), and a heavy chain comprising a heavy chain variable region (VH) which comprises three complementarity determining regions (CDR-H1, CDR-H2 and CDR-H3), wherein the CDR-L1 comprises the amino acid sequence of SEQ ID NO:1, the CDR-L2 comprises the amino acid sequence of SEQ ID NO:2, the CDR-L3 comprises the amino acid sequence of SEQ ID NO:3, the CDR-H1 comprises the amino acid sequence of SEQ ID NO:4, the CDR-H2 comprises the amino acid sequence of SEQ ID NO:5 and the CDR-H3 comprises the amino acid sequence of SEQ ID NO:6.

2. The method according to claim 1, wherein the light chain variable region (VL) comprises the amino acid sequence of SEQ ID No: 7; and the heavy chain variable region (VH) comprises the amino acid sequence of SEQ ID No: 8.

3. The method according to claim 1, wherein said antibody is humanized.

4. The method according to claim 1, wherein said antibody is a murine monoclonal antibody.

* * * * *